(12) United States Patent
Rekdal et al.

(10) Patent No.: US 7,393,824 B1
(45) Date of Patent: Jul. 1, 2008

(54) METHODS OF PEPTIDE PREPARATION

(75) Inventors: Øystein Rekdal, Tromsø (NO); John Sigurd Svendsen, Tromsø (NO); Mari Wikman, Tromsø (NO); Terese Solstad, Tromsø (NO); Nannan Yang, Tromsø (NO)

(73) Assignee: Lytix Biopharma, Tromso (NO)

( * ) Notice: Subject to any disclaimer, the term of this patent is extended or adjusted under 35 U.S.C. 154(b) by 609 days.

(21) Appl. No.: 10/069,613

(22) PCT Filed: Aug. 31, 2000

(86) PCT No.: PCT/GB00/03378

§ 371 (c)(1), (2), (4) Date: Jul. 18, 2002

(87) PCT Pub. No.: WO01/19852

PCT Pub. Date: Mar. 22, 2001

(30) Foreign Application Priority Data

Mar. 9, 2000 (GB) .................................. 0005702.6

(51) Int. Cl.
*A61K 38/00* (2006.01)
*A61K 31/74* (2006.01)

(52) U.S. Cl. ........................................ 514/2; 424/78.04

(58) Field of Classification Search .................. 514/12, 514/2; 435/6; 530/324, 300
See application file for complete search history.

(56) References Cited

U.S. PATENT DOCUMENTS

2003/0022821 A1 * 1/2003 Svenden et al. ............... 514/12

FOREIGN PATENT DOCUMENTS

| WO | WO 96/31537 A1 | 10/1996 |
|---|---|---|
| WO | WO 98/06425 A1 | 2/1998 |
| WO | WO 98/33509 A2 * | 8/1998 |

OTHER PUBLICATIONS

Noble, M. and Dietrich, J. Trends in Neuroscience vol. 27, No. 3, pp. 148-154 Mar. 2004.*
Rekdal et al. Journal of Peptide Science 5: 32-45 (Jan. 1999). "Construction and Synthesis of Lactoferricin Derivatives with Enhanced Antibacterial Activity".*
Javadpour, M. M. et al., "De Novo Antimicrobial Peptides with Low Mammalian Cell Toxicity," *J. Med. Chem.*, 1996, pp. 3107-3113, vol. 39. American Chemical Society.
Johnstone, S.A. et al., "In vitro characterization of the anticancer activity of membrane-active cationic peptides. I. Peptide-mediated cytotoxicity and peptide-enhanced cytotoxic activity of doxorubicin agains,t wild-type and p-glycoprotein over-expressing tumor cell lines," *Anti-Cancer Drug Design*, 2000, pp. 151-160, vol. 15. Oxford University Press.
Shafer, W.M., et al., "Bactericidal Activity of a Synthetic Peptide (CG 117-136) of Human Lysosomal Cathepsin G Is Dependent on Arginine Content," *Infection and Immunity*, Nov. 1996, pp. 4842-4845, vol. 64, No. 11. American Society for Microbiology.
Alvarez-Bravo, J., et al., "Novel synthetic antimicrobial peptides effective against methicillin-resistant *Staphylococcus aureus*," Biochem J., 1994, pp. 535-538, vol. 302. Great Britain.
Dathe, M., et al., "Structural features of helical antimicrobial peptides: their potential to modulate activity on model membranes and biological cells," *Biochimica et Biophysica Acta*, 1999, pp. 71-87, vol. 1462. Elsevier.
Jones, M.K., et al., "Computer programs to identify and classify amphipathic α helical domains," *Journal of Lipid Research*, 1992, pp. 287-296, vol. 33.
Dathe, M., et al., "Hydrophobicitiy, hydrophobic moment and angle subtended by charged residues modulate antibacterial and haemolytic activity of amphiphatic helical peptides," *FEBS Letters*, 1997, pp. 208-212, vol. 403.
Peck-Miller, K.A., "Structure-activity analysis of the antitumor and hemolytic properties of the amphiphilic α-helical peptide, C18G," *Int. J. Peptide Protein Res.*, 1994, pp. 143-151, vol. 44. Belgium.
Maloy, W.L. et al., "Structure-Activity Relationship Studies Around a Decapeptide in Order to Improve Its Therapeutic Index." Poster Extract (P400) from 25th European Peptide Symposium.

* cited by examiner

*Primary Examiner*—Robert B. Mondesi
*Assistant Examiner*—Anand U Desai
(74) *Attorney, Agent, or Firm*—Rothwell, Figg, Ernst & Manbeck

(57) ABSTRACT

The present invention relates to a method of producing a bioactive peptide, wherein the peptide is 7 to 25 amino acids in length, has at least 3 cationic amino acids and is capable of forming an amphipathic α-helix, which method comprises identification of a cationic sector and division of the remaining part of the peptide into three further sectors which are substantially equal in size, and incorporation of at least 60% of the bulk and lipophilicity provided by the amino acid R groups into the sectors flanking the cationic sector; and to uses of the peptides produced thereby in therapy, particularly in the treatment of benign or malignant tumours.

11 Claims, 5 Drawing Sheets

METHODS OF PEPTIDE PREPARATION

The present invention relates to methods of producing bioactive peptides and molecules generated by these techniques. More particularly, the invention relates to bioactive peptides which are capable of forming an α-helical structure in vivo and wherein the relative positions of cationic and bulky and lipophilic residues within the three dimensional structure of the peptide are such as to provide good selectivity and to the production of such peptides. Selectivity, in other words, an exploitable therapeutic window, may be generated or enlarged by increasing the therapeutic activity and/or reducing toxicity.

The invention describes methods for enhancing the activity (antimicrobial or antitumoural) of peptides and of enhancing the selectivity (enlarging the therapeutic window); this may be achieved by increasing the activity while the toxicity is not increased or is increased by a much smaller amount. Alternatively, enhanced selectivity may be achieved by reducing toxicity while activity against target cells remains the same or is only slightly reduced.

Peptides, their derivatives and non-peptide mimics thereof (peptidomimetics) are therapeutically important classes of compounds. Peptides, typically fragments of naturally occurring proteins and peptides, are being developed as antimicrobial particularly antibacterial agents. A wide variety of organisms use peptides as part of their host defence mechanism. Antimicrobial peptides have been isolated from species as diverse as bacteria and mammals [Lehrer, R. I., Lichtenstein, A. K. and Ganz, T. (1993) Ann. Rev. Immunol. 11, 105-128]. Generally, these antibiotic peptides have a net positive charge and a propensity to form amphiphilic α-helix or β-sheet structures upon interaction with the outer phospholipid bilayer in bacterial cell membranes [Besalle, R., Gorea, A., Shalit, J., Metger, J. W., Dass, C. Desiderio, D. M. and Fridkin, M. (1993) J. Med. Chem. 36 1203-1209]. In most cases the detailed molecular mechanisms of the antibiotic action are unknown, although some peptides categorised as class L (lytic) peptides are believed to interact with bacterial cell membranes, probably forming ion-channels or pores [Ludtke, S. J., He, K., Heller, W. T., Harroun, T. A., Yang, L. and Huang, H. W. (1996) Biochemistry 35 13723-13728] leading to permeability changes and consequent cell lysis.

Magainins are antibacterial peptides from the skin of the frog *Xenopus laevis* and are classified as class L antibiotics because they specifically lyse bacteria; other peptides such as mastroparans, a bee venom, lack this specificity as they lyse eukaryotic as well as prokaryotic cells and are called Class L Venoms [Tytler, E. M., Anantharamaiah, G. M., Walker, D. E., Mishra, V. K., Palgunachari, M. N. and Segrest, J. P. (1995) Biochemistry 34 4393-4401].

As well as magainins and mastroparans, host defence peptides have been isolated from moths and flies (cecropins) and from Horseshoe crab. The direct action of these host defence peptides to repel predators, for example as venoms, is clear. The search for peptides which exhibit antibiotic effects has lead to the identification of other proteins/peptides which would not be expected to have cytotoxic properties. One of these is lactoferrin, an iron transporter which also shows a weak antibacterial effect.

As well as searching for new antimicrobial peptides, more recently it has been sought to enhance the activity of proteins or peptides with known antimicrobial properties. This has been done in the case of bovine lactoferrin by digesting the native protein with gastric pepsin to produce a peptide, lactoferricin B (LFB), which is much more active than the native bovine lactoferrin. LFB is a 25 residue peptide which corresponds to residues 17-41 of bovine lactoferrin. [Bellamy et al. (1992) Biochem. Biophys. Acta. 1121 pp 130 et seq.]. Structure-activity studies have been carried out on magainins and it has been shown, for example, that enhancement of helicity and of the cationic charge leads to higher antibacterial activity [Chen, Y. H., Brown, J. H., Morell, J. L. and Huang, C. M. (1988) FEBS Letters 236, 462-466]. However, such sequence modifications often result in higher hemolytic activity. It is thus an object of the present invention to prepare peptides and/or peptide derivatives which have significant antimicrobial activity but preferably have low toxicity, i.e. little effect on normal eukaryotic cells, as exemplified by low hemolytic activity. While red blood cells may not be typical eukaryotic cells, they provide a convenient way of assaying for toxicity and in any event are a type of cell which should not be lysed to a significant extent by therapeutic bioactive peptides.

Structure-activity studies of magainins and other antimicrobial peptides have revealed the importance of a net positive charge, amphipathy and α-helical structure as major structural motifs determining their ability to disrupt membranes (Blondelle 1992, Chen 1988). Attempts have been made to improve the antimicrobial activity and selectivity of such peptides, and the mean hydrophobic moment, a measure of amphiphilicitiy, and hydrophobicity have been investigated (Pathak 1995, Dathe 1997, Wieprecht 1997). Generally, peptides with enhanced hydrophobicity and hydrophobic moments show increased antibacterial activity, but in most cases also increased hemolytic activity. The angle subtended by the positively charged helix has also been investigated (Wieprecht 1997) and it was found that a large angle led to higher antibacterial activity but at the same time reduced selectively.

More recently (e.g. Risso et al. Cell. Immunol. [1998] 107), a role for peptides as anti-cancer drugs, particularly through their ability to lyse tumour cells has been identified. This presents greater problems of selectivity as the target cell as well as surrounding healthy cells are eukaryotic. Identification and enlargement of a therapeutic window in such circumstances is difficult as there are fewer differences between the cell membranes or cell surfaces of target and non-target cells. Tumour cells may vary slightly from their healthy equivalents or from neighbouring eukaryotic cells of different types but these subtle changes are not well understood and thus mechanisms to exploit any differences have not been described. It is therefore a particular object of the present invention to provide a mechanism whereby therapeutic peptides can be identified or developed which have a good antitumoural activity but which have physiologically acceptable levels of toxicity, i.e. do not lyse or otherwise disturb or destroy healthy eukaryotic cells in significant numbers.

Tumours can develop resistance to a broad range of existing chemotherapeutic agents and therefore it would be especially desirable to develop an anti-cancer agent which is active against cells that have developed such a tolerance.

It has surprisingly been found that the spatial relationship between the cationic sector of a peptide and its bulky and lipophilic residues plays a significant role in the peptide's therapeutic activity and/or selectivity.

The present invention is concerned with bioactive peptides which exert their therapeutic effect by interaction with the cell membrane of target cells. Two types of interaction are important in this regard, firstly the positive charge of the peptide which causes it to be attracted to certain negatively charged membrane phospholipids and secondly the presence of bulky and lipophilic groups which it is believed interact with the hydrophobic parts of the phospholipids. Thus, the peptides are amphipathic in nature, having a water loving, positively charged region and a water hating, lipophilic region.

The different side chains of the amino acids which make up the peptide can provide groups with a cationic or lipophilic character. Of the genetically coded amino acids, lysine, arginine and histidine provide cationic moieties, i.e. moieties which are positively charged at pH 7.0 and are thus conveniently referred to herein as cationic amino acids. Of the genetically coded amino acids, valine, leucine, isoleucine, methionine, phenylalanine, tyrosine and tryptophan have bulky and lipophilic side chains and are conveniently referred to herein as bulky and lipophilic amino acids.

The peptides which can be produced according to the methods of the invention are capable of forming an amphipathic α-helical structure in vivo and their amino acid composition and approximate 3-dimensional structure can conveniently be represented by an α-helical wheel, see FIG. 1 by way of example. An α-helix may be left or right 'handed' depending on whether the amino acids are in the D or L form. Both versions are contemplated in the present invention. The helical wheel is a two dimensional representation of a three dimensional peptide, resulting from a notional compression of the peptide in its helical form to a circle. The sectors are thus also considered in two dimensions, their size determined by the angle subtended at the centre of the circle. When plotted in this way one or more cationic sectors, i.e. concentrations of cationic amino acids can be identified. Typically, the peptides which exhibit the desired therapeutic, generally lytic activity, will have one main cationic sector; the cationic sector of the peptide of FIG. 1 is marked by way of example.

The inventors have surprisingly found that concentrating the bulky and lipophilic amino acids in the regions adjacent to the cationic sector enhances both the therapeutic activity and the selectivity of cytotoxic peptides. As discussed in more detail below, this is particularly so when it is desired to maximize the physiological effect of each bulky and lipophilic group. The regions adjacent to the cationic sector have been found to be the most 'active' regions, i.e. the area where the impact of each bulky and lipophilic residue is maximized. Thus, if it is desired to reduce the toxicity of a peptide containing a large number of bulky and lipophilic group while accepting a slightly reduced therapeutic activity, then it may be advantageous to incorporate these residues away from the cationic sector.

In one aspect the present invention provides a method of producing a bioactive peptide, wherein said peptide is 7 to 25, preferably 12 to 25, amino acids in length, has at least 3 cationic amino acids and is capable of forming an amphipathic α-helix, which method comprises identification of a cationic sector and division of the remaining part of the peptide into three further sectors which are substantially equal in size, and incorporation of at least 60%, preferably at least 70%, more preferably at least 80% of the bulk and lipophilicity provided by the amino acid R groups into the sectors flanking the cationic sector.

Hereinafter the sectors flanking the cationic sector are referred to as 'flanking sectors' and the sector opposite the cationic sector as the 'opposite sector'.

Again, as discussed in more detail below, if a peptide has a large number of bulky and lipophilic residues, and/or a large number of cationic groups, it may be preferable to include a lower percentage of bulky and lipophilic residues in the so called flanking sectors.

When the bulky and lipophilic groups are all the same, the % of bulk and lipophilicity will simply equate to the proportion of these bulky and lipophilic groups incorporated into the flanking sectors compared to the total number of such groups in the peptides. Assigning a unit of bulk and lipophilicity to the genetically coded lipophilic amino acids is discussed below, i.e. valine contributes one unit and tryptophan 2 units. In fact, this system can be refined further with the most bulky and lipophilic residue tryptophan being considered to contribute 2.5 units because of its two fused ring structure. R groups which comprise two or more rings which are not fused are more bulky, e.g. biphenylalanine and such groups can be considered to contribute 3 units of bulk and lipophilicity. These principles can be applied to all amino acid R groups, whether they be naturally occurring (but not genetically coded) or modified.

In general amino acids having 3-6 non-hydrogen atoms in their R groups and no cyclic groups will have a unit of 1, amino acids incorporating a single cyclic group and no more than 8 non-hydrogen atoms or a branched alkyl group having 7-9 non-hydrogen atoms in the R group will be assigned 2 units. Two fused rings and a total of 9 to 12 non-hydrogen atoms will contribute 2.5 units and those comprising 2 or more non-fused rings 3 units. Tryptophan and its analogues all are considered to provide 2.5 units.

Alternatively viewed, the present invention provides a method of producing a bioactive peptide, wherein said peptide is 7 to 25, preferably 12 to 25, amino acids in length, has at least 3 cationic amino acids and is capable of forming an amphipathic α-helix, which method comprises identification of a cationic sector and division of the remaining part of the peptide into three further sectors which are substantially equal in size, incorporation into the sector opposite the cationic sector of preferably no more than 2, more preferably no more than 1 bulky and lipophilic amino acids and incorporation into the two sectors flanking the cationic sector of at least 2, preferably 3 or more bulky and lipophilic amino acids.

It should be understood that where reference is made to introduction of at least 2 amino acids into the flanking sectors it is meant that at least 2 bulky and lipophilic amino acids are introduced into the flanking sectors between them, not at least 2 in each flanking sector. Conveniently at least 1 bulky and lipophilic amino acid is present in each sector adjacent to the cationic sector.

Production will involve synthesis of a peptide as defined above, this may conveniently be by transcription and translation of the corresponding nucleic acid sequence, de novo synthesis or modification of an existing peptide. Synthetic methods are discussed in more detail below.

By 'incorporation' is meant inclusion in the sense that the peptide synthesis is performed in such a way that the particular residues are found within the sectors as defined in relation to the produced whole peptide.

Due to their greater bulk and lipophilicity, the peptide will preferably have at least two, e.g. 3 or more residues selected from tyrosine, phenylalanine and tryptophan, tryptophan residues being especially preferred. While the peptide as a whole may have bulky and lipophilic residues selected from the 7 amino acids listed above, the opposite sector will preferably have no more than one, preferably none of the more bulky and lipophilic residues, i.e. tyrosine, phenylalanine and tryptophan or their non-magnetic equivalents.

Viewed from another way, the two groups of bulky and lipophilic amino acids can be considered to contribute 1 or 2 arbitrary 'units' of bulk and lipophilicity respectively, i.e. valine contributes 1 unit and phenylalanine 2 units; tyrosine also contributes 2 units but tryptophan is better considered to contribute 2.5 units. Thus the peptide as a whole will have at least 2 units, preferably at least 3, more preferably 4-8, e.g. 5 or 6 units of bulk and lipophilicity. The opposite sector will thus preferably have no more than 2, preferably 1 or less units of bulk lipophilicity. Generally, as would be expected, longer peptides will require more units of bulk and lipophilicity. Also, peptides incorporating fewer cationic amino acids will require more units of bulk and lipophilicity. Non-genetically coded equivalent amino acids may be similarly grouped; generally, amino acids which have 5 or fewer non-hydrogen atoms in their R group will contribute only 1 unit, these amino acids will typically not contain a cyclic group, while larger groups contribute 2 units and will typically contain a cyclic group. The units contributed by different groups are discussed in more detail above.

Of the genetically coded bulky and lipophilic amino acids, tryptophan is particularly suitable for use in the preparation of peptides according to the present invention. The inventors have observed that peptides incorporating tryptophan have particularly advantageous peptides, i.e. a good therapeutic activity and good selectivity. Toxicity is often measured in terms of a peptide's tendency to lyse erythrocytes but a further important aspect of selectivity is the ability to differentiate between tumour cells and non-tumour cells of a similar type, represented herein by the model of Meth A cells and fibroblasts.

Thus, tryptophan and non-genetically coded analogues and derivatives thereof exhibiting similar 3-dimensional configurations and hydrophobic characteristics are preferred bulky and lipophilic amino acids according to the present invention. Suitable tryptophan derivatives will typically comprise a fused two ring structure, preferably incorporating one 5-membered ring and one 6-membered ring, the 6-membered ring being alkyl or aryl, preferably aryl. Either or both of these rings may be moderately substituted, for example by $C_{1-3}$, preferably $C_{1-2}$ alkyl groups, optionally wherein one or more of the carbon atoms has been replaced by nitrogen, oxygen or sulphur, the ring being substituted by hydroxyl groups or halogens. The imidazole group of tryptophan may alternatively be replaced by a $C_2$ to $C_5$ chained or branched alkyl group, with one or more carbon atoms optionally replaced as discussed above. These tryptophan analogues will all contribute 2.5 units of bulk and lipophilicity.

As discussed above and exemplified in FIG. 2, central to the present invention is the division of the peptide into 4 sectors, the cationic sector, the 2 sectors adjacent to the cationic sector, referred to herein as 'flanking sectors' and the sector opposite the cationic sector, referred to herein as the 'opposite sector'. Such a division has not previously been proposed and surprisingly provides a useful framework for designing new peptides and maximising efficacy and minimising toxicity of known peptides.

Conveniently, the peptide is first represented in the form of an α-helical wheel to facilitate identification of the cationic sector. This can be performed simply by hand involving drawing of the peptide on paper, by modelling including computer modelling, or in any other way.

The production method will therefore generally involve stages of design and synthesis. The design steps may be computer aided and computer programs for e.g. construction of an α-helical wheel are well known in the art; a convenient program is 'Protean and Edit sequence' from DNA Star, Inc. Methods of peptide synthesis are well known in the art and discussed in more detail below.

The techniques described herein are applicable both to the modification of existing peptides, for example to reduce toxicity, enhance selectivity or activity of a known lytic peptide or to the design and synthesis of a new peptide which is intended to have particular therapeutic applications. Thus, as a result of their surprising results relating to the way the relative positions of cationic and bulky/lipophilic amino acids affects activity and selectivity, the inventors have provided a new strategy for the design and synthesis of peptides with a wide range of therapeutic applications. In particular, the strategy is of use in the design and synthesis of lytic peptides which target microbial or tumour cells.

The surprisingly good selectivity of these peptides makes them particularly effective as anti-tumour peptides. The present invention thus enables an amphipathic helical peptide with low toxicity to be modified by addition of bulky and lipophilic amino acids or repositioning of the native bulky and lipophilic residues to give enhanced tumoricidal activity and selectivity.

The present invention is concerned with optimising the therapeutic impact of the bulky and lipophilic groups found within the peptide. It has generally been found that the greater the overall bulk of a peptide, e.g. the larger the number of bulky and lipophilic groups or the higher the number of units of bulk and lipophilicity present, the more active the peptide both therapeutically and toxically. Thus there is a desire to make the best use of the bulky groups to maximise therapeutic activity and minimise toxic effects, the present invention addresses this need.

This need may be particularly acute when it is important to achieve a useful therapeutic effect but retain very low in vivo toxicity, as is often the case when treating children or cancer patients weakened by their cancer and/or the treatments they have received. Maximising the effect of a small number of bulky and lipophilic groups may also be important in certain drug delivery systems, e.g. where it is desired to minimise the size and/or hydrophobicity of the administered peptide. It may also be beneficial to keep the number of lipophilic residues to a minimum as a higher number may decrease the α-helicity of the peptide, e.g. Ala has a much higher α-helical stabilizing effect than large lipophilic groups.

Peptides prepared by methods which include the production method defined above constitute a further aspect of the present invention. It will be understood that such peptides may have been further modified after the steps described above have been performed. Thus, in a further aspect, the present invention provides a method for the production of a pharmaceutical composition comprising the method of peptide production defined herein and furthermore, mixing the compound prepared thereby or a derivative thereof with a pharmaceutically acceptable carrier.

In a further aspect, the invention provides a process for the preparation of an antibacterial or anti-tumoural agent comprising identifying a peptide which is 7 to 25 amino acids in length, has at least 3 cationic amino acids, is capable of forming an amphipathic α-helix, has no more than 2 bulky and lipophilic groups in the sector opposite the cationic sector and at least two bulky and lipophilic groups in the sectors flanking the cationic sector, synthesising said peptide or a derivative or non-peptide biomimetic thereof, and optionally formulating said peptide, derivative or biomimetic into a physiologically acceptable carrier or excipient. Alternatively viewed, the identified peptide is 7 to 25 amino acids in length etc. and has at least 60%, preferably at least 70%, more preferably at least 80% of the bulk and lipophilicity provided by the amino acid R groups in the flanking sectors.

The identification process may involve aspects of design and modification of a peptide, either de novo or based on a known peptide where the aim is to enhance activity and or selectivity of that known peptide. The process may involve in vitro or in vivo testing of the peptide, followed where necessary or desirable by further modifications within the parameters defined herein and synthesis and re-testing before optional formulation into a pharmaceutical composition. The process may involve identification of a peptide, testing the bioactivity of that peptide and synthesis of a non-peptide derivative or mimetic thereof for formulation.

An important step is the identification of the cationic sector. The cationic sector will comprise at least two cationic amino acids, preferably 3 or 4 or more cationic residues. Not all the amino acids within the cationic sector will be cationic in nature but the cationic sector will contain no more than two non-cationic amino acids, preferably no more than one cationic amino acid. An unmodified N-terminal amino acid is considered a 'cationic amino acid' because the N-terminus is positively charged at pH 7.0, unless it has an anionic R group in which case it is no longer considered a cationic amino acid.

The cationic sector will therefore be that sector which incorporates the most number of cationic amino acids but which has a maximum of 2 non-cationic amino acids. Identification of cationic sectors within peptides, particularly those which form an amphipathic α-helix is a technique well known to the man skilled in the art.

The angle of the cationic sector will generally vary from 200 to 60°, preferably from 180 to 90°. A peptide when depicted in the α-helical wheel format (also called a helical wheel projection) may have more than one cluster of cationic residues, i.e. more than one 'cationic sector'. In this case, the main cationic sector, i.e. the sector with the largest number of cationic amino acids is considered to be the cationic sector for the purposes of the present invention.

The cationic sector will preferably encompass at least half of all the cationic amino acids in the peptide. Preferably 60%, more preferably 70%, e.g. 80% or more of all cationic residues will be in the cationic sector. The requirement that the peptide can form and be classed as an amphipathic α-helix in any case requires there to be a certain pattern and concentration of different types of residues as is appreciated by the skilled man.

If the cationic sector has an angle of 180° for example, the flanking and opposite sectors will all have an angle of 60°. Thus, for a peptide with 12, 18 or 24 amino acids, each of these three sectors will have 2, 3 or 4 residues respectively. (The cationic sector will have 6, 9 or 12 amino acids in each case.) Clearly the number of amino acids in the non-cationic part of the peptide will not always be readily devisable by three to delineate the other three sectors. In this case, the two flanking sectors will always have the same number of residues while the opposite sector may have one more or one less residue than the two flanking sectors. Thus it is appropriate to refer to the three sectors other than the cationic sector as being substantially equal in size as it will not always be possible for them to be exactly equal in size.

The peptides will preferably have 12 or more amino acids, e.g. be 12 to 21 amino acids in length.

The inventors have shown that in order to exhibit desirable antimicrobial and/or antitumoural activity, it is the position within the 3-dimensional structure of the bulky and lipophilic amino acids as much as the number of such residues which is important. In particular, it has been shown that preferred peptides are those which do not have a significant number of bulky and lipophilic residues in the region opposite the cationic sector; this seems to aid selectivity either by enhancing activity or by reducing toxicity. Considered another way, preferred peptides are those in which the majority of bulky and lipophilic residues are in the regions adjacent to the cationic sector.

Peptides having enhanced antibacterial and/or antitumoural activity and preferably reduced toxicity can be prepared by moving a bulky and lipophilic amino acid from its position in the original/native sequence to a region adjacent to the cationic sector, thus the overall amino acid composition of the peptide remains unchanged. Such 7-25 mer peptides which have 3 or more cationic residues and are capable of forming an amphipathic α-helix and which have an extra bulky and lipophilic amino acid adjacent to the cationic sector, said extra bulky and lipophilic amino acid being taken from another, non-preferred, position in the sequence constitute a further aspect of the present invention. In place of the bulky and lipophilic amino acid can be put the residue from the position adjacent to the cationic sector which the bulky and lipophilic amino acid replaces or any other less bulky and lipophilic amino acid. Suitable bulky and lipophilic amino acids in non-preferred positions which can be moved into the region adjacent to the cationic sector (preferred position) can be identified by e.g. an alanine scan which identifies non-essential amino acids or by studying a helical wheel arrangement, non-preferred positions typically being opposite a cationic domain.

In a variation of the above described modification, a bulky and lipophilic amino acid is taken from a non-preferred position, preferably in the opposite sector and something which is functionally equivalent to it is placed in a preferred position, i.e. in a flanking sector. Thus the residue newly positioned in the flanking sector will be bulky and lipophilic but may be e.g. tryptophan or a modified or non-genetically coded amino acid, whereas the replaced residue in the cationic sector was phenylalanine. The bulky and lipophilic character of the residue thus being more important than its precise structure.

While a minimum number of bushy and lipophilic amino acids is required for good activity, their position relative to the cationic sector may determine whether the peptide has good activity and is selective for the target cells, i.e. has low toxicity. For peptides of 19 amino acids or more generally at least 7.5 units of bulk and lipophilicity in total will be required (e.g. three Trp residues or equivalent), peptide of 12 to 18 residues in length may require few units, typically 5 or more. The optimum number of units will more importantly also depend on the number of cationic residues present, with fewer units being required when more cationic residues are present. For example, 7.5 units in the flanking sectors may be optimum when the peptide has 8-10 cationic residues but 10 units may be preferred for peptides having 6 or 7 cationic residues.

Thus, a method of enhancing the activity of a known peptide is provided wherein bulky and lipophilic amino acids are rearranged to be in the position which the inventors have shown to improve the activity profile of the peptide as a whole. Typically this will involve relocation from the opposite sector to a flanking sector. As discussed above, this may mean that the overall amino acid composition of the peptide remains unchanged. More particularly, this means that the overall number of bulky and lipophilic residues in the modified peptide may be the same as in the stating sequence. The stating sequence may be a naturally occurring peptide or a fragment of a naturally occurring peptide or a peptide designed or modified to provide antimicrobial or other activity.

Amino acids of the same type, cationic, bulky and lipophilic (which are defined above) anionic (aspartic and glutamic acid) or within the following functional groupings, glycine and alanine or serine, threonine, asparagine, glutamine and cysteine can be replaced by other residues within that class without altering the functional composition of the peptide, proline can be considered to be in a class of its own and is generally a non-preferred component of the peptides of the invention. Non-genetically coded amino acids which fall within these functional groupings are readily available and known to the skilled man.

In certain circumstances, as well as removing a bulky and lipophilic amino acid from the opposite sector and introducing a bulky and lipophilic amino acid into an adjacent sector, a modification which alters the functional composition of the stating peptide may be made. For example, the number of cationic or bulky and lipophilic residues may be increased.

This aspect of the invention relates to a 'shuffling' of existing residues within the peptide to optimise activity, such that the number of residues within each functional category remains the same or nearly the same. This can be considered a functional homology which is dependent on the composition and not the specific order of the sequence and where amino acids in the different classes are functionally the same. Thus the tri-peptide Arg-Trp-Ala has a 100% functional homology with Phe-Lys-Gly. In relation to this aspect of the invention, the peptides will have at least a 70%, preferably an 80%, even 90 or 100% functional homology with a known or naturally occurring peptide which exhibits some antimicrobial or antitumoural activity.

For convenience, the well known amino acid three letter and one letter codes are used herein.

Suitable peptides which can be modified to provide peptides in accordance with the invention include all peptides such as the magainins, PGLa analogues, cecropins, defensins, melittin and lactoferrin, and class (L) lytic peptides generally etc. which are known in their unmodified form to exhibit cytotoxic, particularly anti-microbial activity. Further suitable peptides include those which are not naturally occurring but have been synthesised and exhibit cytotoxic activity, such peptides include the modelines. In this context, the pre-modification peptides include fragments obtained by digestion of naturally occurring proteins or peptides. New anti-bacterial proteins and peptides are still being discovered and it is believed that the techniques of the present invention have general applicability and could be applied simply, and with a reasonable chance of success, to peptides which are as yet unidentified but are subsequently characterised as cytotoxic, particularly as antimicrobial.

In the case of anti-tumoural agents, good selectivity is both particularly important and difficult to achieve due to the similarities between target and non-target cells. It has been found that peptides having reduced toxicity but still having reasonable antibacterial or anti-tumoural activity (i.e. having enhanced selectivity) may be prepared by replacing a non-essential highly bulky and lipophilic amino acid such as tryptophan or phenylalanine with a less bulky and lipophilic amino acid e.g. isoleucine or leucine or even alanine or lysine. Generally, a "non-essential" bulky and lipophilic amino acid will be positioned on the opposite side of the helix from the cationic sector (i.e. in the opposite sector), such non-essential bulky and lipophilic amino acids can be identified using a helical wheel diagram or by an alanine scan. These peptides should nevertheless retain at least 2, preferably at least 3 bulky and lipophilic amino acids as herein defined. In terms of units of bulk and lipophilicity, the peptides will preferably have at least 5, preferably at least 7 e.g. 7.5 or more units of bulk and lipophilicity which is preferably found in the sectors adjacent to the cationic sector.

Thus, modified cytotoxic peptides having 7 to 25 amino acids, at least three cationic residues and at least two bulky and lipophilic amino acids and being capable of forming an amphipathic α-helix, wherein one non-essential tryptophan or phenylalanine residue in the original/native sequence is replaced by a less bulky and lipophilic residue e.g. isoleucine or alanine constitute a further aspect of the present invention. Indolici(di)n is a naturally occurring tryptophan rich peptide which may conveniently be modified in this way to reduce its toxicity. The hemolytic activity of a peptide may conveniently be reduced in this way. Toxicity as measured by a tendency to inhibit or lyse fibroblast cells may be reduced by replacing a bulky and lipophilic group in an opposite sector with a residue which is not bulky and lipophilic e.g. alanine.

Other suitable sites for incorporation of a bulky and lipophilic amino acid are positions at or near, preferably adjacent, to an existing lipophilic amino acid. Proximity is judged in terms of the secondary rather than primary structure of the peptide. The techniques involved in performing an alanine scan and in constructing helical wheel diagrams are well known in the art.

Particularly interesting effects with regard to selectivity have been observed with peptides incorporating one or more two-fused-ring bulky and lipophilic groups such as tryptophan. Amino acid R groups consisting of two-fused-rings having little or no substitution generally contribute 2.5 units of bulk and lipophilicity as discussed above. The effects have been investigated with a series of model peptides based on a $(KAAKKAA)_3$ sequence. It has been shown that for peptides incorporating 3 tryptophan residues, these should be positioned in the sectors adjacent to the cationic sector. If such a peptide contains 4 tryptophan residues, these should be placed either in the opposite sector or in the regions of the flanking sectors which are not directly adjacent to the cationic sector.

This indicates that a peptide will have a threshold of bulk and lipophilicity above which it is desirable to place bulky and lipophilic residues away from the most 'active' regions of the peptide, i.e. those which are adjacent, especially directly adjacent to the cationic sector. As will be appreciated by the skilled man, this threshold will vary depending on the length of the peptide, but more particularly on the number of cationic residues and the degree of bulk and lipophilicity exhibited by the various groups.

Tryptophan is particularly useful in the design of peptides incorporating good selectivity for tumour cells because it is naturally occurring and therefore may be incorporated in a process which relies on transcription and translation of the peptide product, e.g. by bacterial fermentation systems. Also it may be readily metabolised by the body without giving rise to potentially dangerous toxic breakdown products.

Nevertheless, it is understood that peptides may be prepared by 'synthetic' routes which do not rely on the normal mechanisms of transcription and translation and in these molecules non-genetically coded amino acids may be incorporated. In addition peptides produced e.g. by bacteria may undergo post-translational modifications. Thus, the peptides produced according to the present invention will preferably incorporate one or more amino acids having two-fused-ring R groups, such as tryptophan residues or analogues thereof.

Tryptophan analogues are a group of molecules which exhibit similar three dimensional structures to tryptophan as well as similar properties in terms of lipophilicity and polarity. Lipophilicity may be measured in several different ways which are known in the art, in particular is the experimental determination of a partition coefficient in a water: octanol system. The partition coefficient P (or Log P) is defined as the concentration of a compound in the octanol phase divided by the concentration in the water phase. The indole group of Trp has a Log P of 2.14 and the side chain of Trp analogues will preferably have Log P values of 1.5 to 3.5, more preferably 1.8 to 2.5. These analogues will incorporate a two-fused ring structure, one ring preferably being an aromatic $C_6$ ring e.g. as in benzo-thienylalanine, the second ring may be a 5 or 6-membered ring which may conveniently also be aromatic e.g. as in 2 or 1-naphthylalanine or a 5- or 6-membered non-aromatic group wherein one or more carbon atoms are optionally replaced by oxygen, nitrogen or sulphur. The two-fused rings may be substituted by methyl, hydroxy or halogens groups but will preferably be unsubstituted.

For those peptides with smaller cationic sectors e.g. the 15 mer peptide KKWAKKAWKWAKKAW which has only 7 residues forming the cationic sector as opposed to 9 residues in the 21 mer peptide described above, a greater degree of bulk and lipophilicity is desirable for optimum therapeutic activity and selectivity and four tryptophan residues present in the flanking regions gave excellent results. Thus there is a balance, if a peptide is highly cationic and thus has a very strong attraction for negatively charged phospholipids in the cell membranes, a smaller overall number of bulky and lipophilic groups are desirable for optimum selectivity or it may be necessary to place some of the bulk and lipophilicity in the less active regions, i.e. in the regions opposite the cationic sector, in order to reduce the impact of the bulky and lipophilic groups e.g. to reduce toxicity. If a molecule has fewer cationic residues, then it may be necessary to place all the bulky and lipophilic residues in the most active regions of the peptide adjacent to the cationic sector. The results and principles discussed herein enable the skilled man to optimise the activity and selectivity of his chosen peptide system.

Thus, in a further aspect, the present invention provides a method of producing a bioactive peptide, wherein said peptide is 7 to 25, preferably 12 to 25, amino acids in length and is capable of forming an amphipathic α-helix, which method comprises identification of a cationic sector and division of the remaining part of the peptide into three further sectors which are substantially equal in size, and (a) for a peptide having 4 to 8 e.g. 5 to 7 cationic residues, incorporation into the sectors flanking the cationic sector of at least 3, preferably 4, amino acids having two-fused-ring R groups (e.g. tryptophan residues or analogues thereof), or (b) for a peptide having 8, usually 9 or more cationic residues (e.g. 9-12 cationic residues), incorporation into the sectors flanking the cationic sector of 2 to 4, preferably 3 amino acids having two-fused-ring R groups (e.g. tryptophan residues or analogues thereof), or (c) for a peptide having 8, usually 9 or more cationic residues, incorporation into the sector opposite the cationic sector of 4 or 5, preferably 4, amino acids having two-fused-ring R groups, or incorporation of 2 amino acids having two-fused-ring R groups into each of the two sectors flanking the cationic sector wherein no more than one, preferably none of these amino acids is in a position actually adjacent to the cationic sector.

In case (b) described above, when only two amino one further amino acid having a two-fused-ring R group is preferably incorporated into the sector opposite the flanking sector.

The peptides of the examples, particularly those which have a Fib $IC_{50}$/Meth A $IC_{50}$ ratio (see Example 3) of greater than 10, preferably greater than 15 constitute a further aspect of the present invention. These peptides are examples of a class of active peptides, which constitute a further aspect of the invention, i.e. a cytotoxic 12 to 25 mer, preferably 14 to 22 mer peptide which when represented as a 2 dimensional helical wheel has a cationic sector comprising at least 5, preferably at least 6, more preferably at least 7 or 8, particularly preferably 9 or 10 cationic residues, said peptide having a Fib $IC_{50}$/Meth A $IC_{50}$ ratio of greater than 10, preferably greater than 15, more preferably greater than 18, especially preferably greater than 20. Where appropriate this particular selectivity ratio can be substituted by an equivalent $IC_{50}$ non-malignant/tumour cell ratio for the target tumour cells of interest, see for example Johnstone, S. A. et al. in Anti-Cancer Drug Design (2000) 15, 151-160.

Conveniently, the remaining part of the peptide is divided into three further sectors of substantially equal size, said peptide preferably incorporating 2, more preferably 3 tryptophan residues or analogues thereof in the flanking sectors, at least one and preferably 2 of these residues being immediately adjacent to the cationic sector; or having 5 or preferably 4 tryptophan residues or analogues thereof in the opposite sector to the cationic sector; or 4 or 5 residues split between the three non-cationic sectors provided none of these residues are in the positions exactly adjacent is the cationic sectors. Preferably no more than one, more preferably none of these residues are only one position from the cationic sector (assuming the overall size of the peptide allows for this). The are only one position from the cationic sector (assuming the overall size of the peptide allows for this). The remaining residues are preferably selected from glycine, alanine and valine, preferably glycine or alanine.

It has further been observed that for very large bulky and lipophilic amino acids e.g. biphenylalanine the position within the helical wheel is of less importance, peptides having amino acids which each contribute 3 units of bulk and lipophilicity may exhibit good selectivity whether they are positioned in the flanking or opposite sectors. Such cytotoxic 7-25, preferably 12-25 mer peptides, incorporating 5-11 cationic residues and 2-4 amino acids having two non-fused-ring R groups but the degree of selectivity discussed above, e.g. an $IC_{50}$ non-malignant/tumour cell ratio of greater than 10, constitute a further aspect of the present invention. Methods of producing such peptides constitute a yet further aspect of the present invention. In place of 2-4 two non-fused ring R groups may be found 4 to 8 small bulky and lipophilic groups, i.e. those which contribute no more than 2 units of bulk and lipophilicity, e.g. having only one cyclic group in the amino acid R group such as phenylalanine.

In the case of LFB(17-31), a 15 amino acid fragment of LFB having the sequence Phe-Lys-Cys-Arg-Arg-Trp-Gln-Trp-Arg-Met-Lys-Lys-Leu-Gly-Ala, non-essential amino acids determined using an alanine scan were Cys(3), Gln(7) and Gly(14), here the numbering is in absolute terms relating to the peptide itself. Analogs of LFB(17-31) wherein these amino acids are replaced by non-genetic bulky and lipophilic amino acids may be particularly effective. For modifications to magainin peptides such as magainin 2, incorporation of non-genetic bulky and lipophilic amino acids at positions Phe(16) and Glu(19) may be particularly effective.

These modifications illustrate the general principles discussed above, that the peptide can be considered to comprise different sectors and, surprisingly, the region adjacent to the cationic sector is a preferred region for bulky and lipophilic residues and moreover the region opposite the cationic sector should contain few or no bulky and lipophilic residues.

The tryptophan replacements in Example 2 indicate the importance of having a bulky and lipophilic residue, here Trp in the regions adjacent to the cationic sector for both therapeutic (cyclic activity against Meth A cells) and selectivity, i.e. ability to target tumour cells rather than fibroblasts or red blood cells. As can be seen from FIG. 1, position 3 is opposite the cationic sector and positions 9 and 11 are adjacent to the cationic sector.

In a preferred embodiment of the present invention, the opposite sector will incorporate a hydrophilic residue e.g. lysine, arginine or equivalent.

It should be understood that all the peptides of the invention disclosed herein may incorporate non-genetically coded amino acids and peptides which have been modified, e.g. at the N or C terminus, typically by amidation or esterification of the C terminus. Thus, bulky and lipophilic and cationic amino acids may be provided by non-genetically coded but naturally occurring amino acids by non-naturally occurring amino acids or amino acids which have been modified. Examples of non-genetic bulky and lipophilic amino acids include adamantylalanine, 3-benzothienylalanine, 4,4'-biphenylalanine, 3,3-diphenylalanine, homophenylalanine, 2,6-dichlorobenzyltyrosine, cyclohexyltyrosine, 7-benzyloxytryptophan, tri-tert-butyltryptophan, homotryptophan, 3-(-anthracenyl)-L-alanine, L-p-iso-propylphenylalanine, L-thyroxine, 3,3',5-triiodo-L-thyronine. Modifying groups which provide bulky and lipophilic amino acids include Pmc (2,2,5,7,8-pentamethylchroman-6-sulphonyl), Mtr (4-methoxy-2,3,6-trimethylbenzenesulfonyl) and Pbf (2,2,4,6,7-pentamethyldihydrobenzofuransulfonyl), which may conveniently increase the bulk and lipophilicity of aromatic amino acids, e.g. Phe, Trp and Tyr. Also, the tert-butyl group is a common protecting group for a wide range of amino acids and is capable of providing non-genetic bulky and lipophilic amino acids, particularly when modifying aromatic residues. The Z-group (carboxybenzyl) is a further protecting group which can be used to increase the bulk and lipophilicity of an amino acid.

In addition, the present invention relates to non-peptide compounds showing the same cytotoxic activity as their proteinaceous counterparts. Such peptidomimetics or "small molecules" capable of mimicking the activity of a protein or peptide are likely to be better suited for e.g. oral delivery due to their increased chemical stability. Such compounds will also have a substantially helical structure in vivo, or be capable of forming such a structure when in contact with cell membranes. They will thus also have a cationic part and regions corresponding to the different sectors discussed above.

It is now commonplace in the art to replace peptide or protein-based active agents e.g. therapeutic peptides with such peptidomimetics having functionally-equivalent activity. Generally such compounds will simply replace the $-(C(R)CONH-)_n$ backbone of the peptide with an alternative flexible linear backbone, e.g. a $-(C(R)NHCO-)_n$ or $-(C(R)CH_2CH_2-)_n$, or a non-linear backbone (e.g. one based on a string of fused cyclohexane rings). Despite the change in the backbone, the pendant functional groups (the side chains in the peptide original) are presented in a similar fashion allowing the compound to possess similar antibacterial and antitumoral activities. Typically therefore, the peptidomimetic is capable of representation on the equivalent of an α-helical wheel and will show the equivalent helical/cylindrical display of pendant functional groupings.

Various molecular libraries and combinatorial chemistry techniques exist and are available to facilitate the identification, selection and/or synthesis of such compounds using standard techniques (Kieber-Emons, T. et al. Current Opinion in Biotechnology 1997 8: 435-441). Such standard techniques may be used to obtain the peptidomimetic compounds according to the present invention, namely peptidomimetic organic compounds which show substantially similar or the same cytotoxic activity as the peptides of the invention, e.g. as described herein in the Examples.

A further aspect of the invention thus provides a biomimetic organic compound based on the peptides of the invention, characterised in that said compound exhibits cytotoxic, e.g. antibacterial or antitumoural activity, at least the level exhibited by the peptides of the invention as hereinbefore defined.

Thus, in one embodiment is provided a method of producing a biomimetic molecule which is equivalent to 7 to 25 amino acids and has groups equivalent to 3 cationic amino acids and is capable of forming an amphipathic α-helix, which method comprises identification of a cationic sector and division of the remaining part of the molecule into three further sectors which are substantially equal in size, incorporation into the sector opposite the cationic of no more than 2, preferably no more than 1 group equivalent to a bulky and lipophilic amino acid R groups and incorporation into the two sectors flanking the cationic sector of at least 2, preferably 3 or more of said bulky and lipophilic groups in total.

Alternatively viewed, the invention provides a method of producing a biomimetic molecule which is equivalent to 7 to 25 amino acids and has groups equivalent to at least 3 cationic amino acids and is capable of forming an amphipathic α-helix, which method comprises identification of a cationic sector and division of the remaining part of the molecule into three further sectors which are substantially equal in size, and incorporation of at least 60%, preferably at least 70%, more preferably at least 80% of the bulk and lipophilicity provided by the amino acid R groups into the sectors flanking the cationic sector.

The term "cytotoxic" is intended to refer not only to an activity against prokaryotic cells but also against eukaryotic cells. Although in certain circumstances it is desirous to have a peptide which has a good anti-bacterial activity but does not lyse or otherwise destroy the cells of the patient, peptides within the scope of the present invention have been shown to have an anti-tumoural activity. The anti-tumoural activity of these peptides and medicaments containing them constitute further aspects of the present invention. Anti-tumoural activity includes the destruction or reduction in size or number of benign or malignant tumours and the prevention or reduction of metastasis.

Thus, peptides produced by the methods of the invention for use in therapy, particularly the destruction or reduction in size or number of benign or malignant tumours or the prevention of reduction of metastasis constitutes a further aspect of the invention. Likewise, use of peptides produced by the methods of the invention in the manufacture of a medicament for the destruction or reduction in size or number of benign or malignant tumours or the prevention of reduction of metastasis constitutes a further aspect of the present invention.

The antibacterial activity of the peptides of the invention may manifest itself in a number of different ways. Certain modifications may result in peptides which are bacteriostatic and others in peptides which are bacteriocidal. Advantageously, the majority of the peptides according to the invention are bactericidal. Thus, inter alia, the invention also provides a method of inhibiting the growth of bacteria comprising contacting the bacteria with an inhibiting effective amount of a bioactive peptide according to the invention.

The term "contacting" refers to exposing the bacteria to a peptide so that it can effectively inhibit, kill or lyse bacteria, bind endotoxin (LPS), or, permeabilize gram-negative bacterial outer membranes. Contacting may be in vitro, for example by adding the peptide to a bacterial culture to test for susceptibility of the bacteria to the peptide. Contacting may be in vivo, for example administering the peptide to a subject with a bacterial disorder, such as septic shock. "Inhibiting" or "inhibiting effective amount" refers to the amount of peptide which is required to cause a bacteriastatic or bacteriacidal effect. Examples of bacteria which may be inhibited include E. coli, P aeruginosa, E. cloacae, S. typhimurium and S. aureus. The method of inhibiting the growth of bacteria may further include the addition of antibiotics for combination or synergistic therapy. The appropriate antibiotic administered will typically depend on the susceptibility of the bacteria such as whether the bacteria is gram negative or gram positive, and will be easily discernable by one of skill in the art.

The peptides of the invention may be directly synthesised in any convenient way. Generally the reactive groups present (for example amino, thiol and/or carboxyl) will be protected during overall synthesis. The final step in the synthesis will thus be the deprotection of a protected derivative of the invention.

In building up the peptide, one can in principle start either at the C-terminal or the N-terminal although the C-terminal starting procedure is preferred. The non-genetic amino acid can be incorporated at this stage as the sequence is extended or as a result of a post-synthetic modification.

Methods of peptide synthesis are well known in the art but for the present invention it may be particularly convenient to carry out the synthesis on a solid phase support, such supports being well known in the art.

A wide choice of protecting groups for amino acids are known and suitable amine protecting groups may include carbobenzoxy (also designated Z) t-butoxycarbonyl (also designated Boc), 4-methoxy-2,3,6-trimethylbenzene sulphonyl (Mtr) and 9-fluorenylmethoxycarbonyl (also designated Fmoc). It will be appreciated that when the peptide is built up from the C-terminal end, an amine-protecting group will be present on the α-amino group of each new residue added and will need to be removed selectively prior to the next coupling step.

Carboxyl protecting groups which may, for example be employed include readily cleaved ester groups such as benzyl (Bzl), p-nitrobenzyl (ONb), pentachlorophenyl (OPClP), pentafluorophenyl (OPfp) or t-butyl (OtBu) groups as well as the coupling groups on solid supports, for example methyl groups linked to polystyrene.

Thiol protecting groups include p-methoxybenzyl (Mob), trityl (Trt) and acetamidomethyl (Acm).

A wide range of procedures exists for removing amine- and carboxyl-protecting groups. These must, however, be consistent with the synthetic strategy employed. The side chain protecting groups must be stable to the conditions used to remove the temporary α-amino protecting group prior to the next coupling step.

Amine protecting groups such as Boc and carboxyl protecting groups such as tBu may be removed simultaneously by acid treatment, for example with trifluoroacetic acid. Thiol protecting groups such as Trt may be removed selectively using an oxidation agent such as iodine.

A particularly preferred method involves synthesis using amino acid derivatives of the following formula: Fmoc-amino acid-Opfp.

The present invention also provides pharmaceutical compositions containing the peptides of the invention as defined above together with a physiologically acceptable diluent, carrier or excipient. Suitable diluents, excipients and carriers are known to the skilled man. The peptides of the invention for use in methods of treatment particularly in the treatment or prevention of bacterial infections or as an anti-tumour agent, both in the destruction or reduction in size or number of benign or malignant tumours which may be ascites and in the prevention of metastasis constitute further aspects of the present invention.

The compositions according to the invention may be presented, for example, in a form suitable for oral, nasal, parenteral, intravenal, intratumoral or rectal administration.

As used herein, the term "pharmaceutical" includes veterinary applications of the invention.

The compounds according to the invention may be presented in the conventional pharmacological forms of administration, such as tablets, coated tablets, nasal sprays, solutions, emulsions, liposomes, powders, capsules or sustained release forms. The peptides of the invention are particularly suitable for topical administration, e.g. in the treatment of diabetic ulcers. Conventional pharmaceutical excipients as well as the usual methods of production may be employed for the preparation of these forms. Tablets may be produced, for example, by mixing the active ingredient or ingredients with known excipients, such as for example with diluents, such as calcium carbonate, calcium phosphate or lactose, disintegrants such as corn starch or alginic acid, binders such as starch or gelatin, lubricants such as magnesium stearate or talcum, and/or agents for obtaining sustained release, such as carboxypolymethylene, carboxymethyl cellulose, cellulose acetate phthalate, or polyvinylacetate.

The tablets may if desired consist of several layers. Coated tablets may be produced by coating cores, obtained in a similar manner to the tablets, with agents commonly used for tablet coatings, for example, polyvinyl pyrrolidone or shellac, gum arabic, talcum, titanium dioxide or sugar. In order to obtain sustained release or to avoid incompatibilities, the core may consist of several layers too. The tablet-coat may also consist of several layers in order to obtain sustained release, in which case the excipients mentioned above for tablets may be used.

Organ specific carrier systems may also be used.

Injection solutions may, for example, be produced in the conventional manner, such as by the addition of preservation agents, such as p-hydroxybenzoates, or stabilizers, such as EDTA. The solutions are then filled into injection vials or ampoules.

Nasal sprays which are a preferred method of administration may be formulated similarly in aqueous solution and packed into spray containers either with an aerosol propellant or provided with means for manual compression. Capsules containing one or several active ingredients may be produced, for example, by mixing the active ingredients with inert carriers, such as lactose or sorbitol, and filling the mixture into gelatin capsules.

Suitable suppositories may, for example, be produced by mixing the active ingredient or active ingredient combinations with the conventional carriers envisaged for this purpose, such as natural fats or polyethyleneglycol or derivatives thereof.

Dosage units containing the compounds of this invention preferably contain 0.1-10 mg, for example 1-5 mg of the peptides of the invention. The pharmaceutical compositions may additionally comprise further active ingredients, including other cytotoxic agents such as other antimicrobial peptides. Other active ingredients may include different types of antibiotics, cytokines e.g. IFN-γ, TNF, CSF and growth factors, immunomodulators, chemotherapeutics e.g. cisplatin or antibodies.

A yet further aspect of the present invention provides the therapeutic use of the peptides of the invention as defined above i.e. the peptides for use as medicaments, e.g. antibacterions or antitumoural agents. Further aspects comprise a method of treating or preventing bacterial infections in a patient comprising the administration to said patient of one or more of the peptides of the invention and a method of treating tumours in a patient comprising the administration of one or more of the peptides of the invention. The treatment of tumours includes the destruction or reduction in size or number of benign or malignant tumours which may be ascites and the prevention of metastasis.

A still further aspect of the present invention comprises the use of one or more of the peptides of the invention in the manufacture of a medicament for treating bacterial infections or tumours.

Anti-bacterial agents such as the peptides of the present invention have a wide variety of applications other than as pharmaceuticals. They can be used, for example, as sterilising agents for materials susceptible to microbial contamination. The peptides of the invention exhibit broad antimicrobial and antibiotic activity and thus are also suitable as anti-viral and anti-fungal agents which will have pharmaceutical and agricultural applications and as promoters of wound healing or spermicides. All of these uses constitute further aspects of the invention.

The peptides, when used in topical compositions, are generally present in an amount of at least 0.1%, by weight. In most cases, it is not necessary to employ the peptide in an amount greater than 1.0%, by weight.

Anti-tumour peptides may be administered in combination, possibly in synergistic combination with other active agents or forms of therapy, for example administration of a peptide according to the invention may be combined with chemotherapy, immunotherapy, surgery, radiation therapy or with the administration of other anti-tumour peptides.

In employing such compositions systemically (intra-muscular, intravenous, intraperitoneal), the active peptide is present in an amount to achieve a serum level of the peptide of at least about 5 ug/ml. In general, the serum level of peptide need not exceed 500 ug/ml. A preferred serum level is about 100 ug/ml. Such serum levels may be achieved by incorporating the peptide in a composition to be administered systemically at a dose of from 1 to about 10 mg/kg. In general, the peptide(s) need not be administered at a dose exceeding 100 mg/kg.

The invention will now be described with reference to the following non-limiting examples in which.

EXAMPLES

Figure 1:
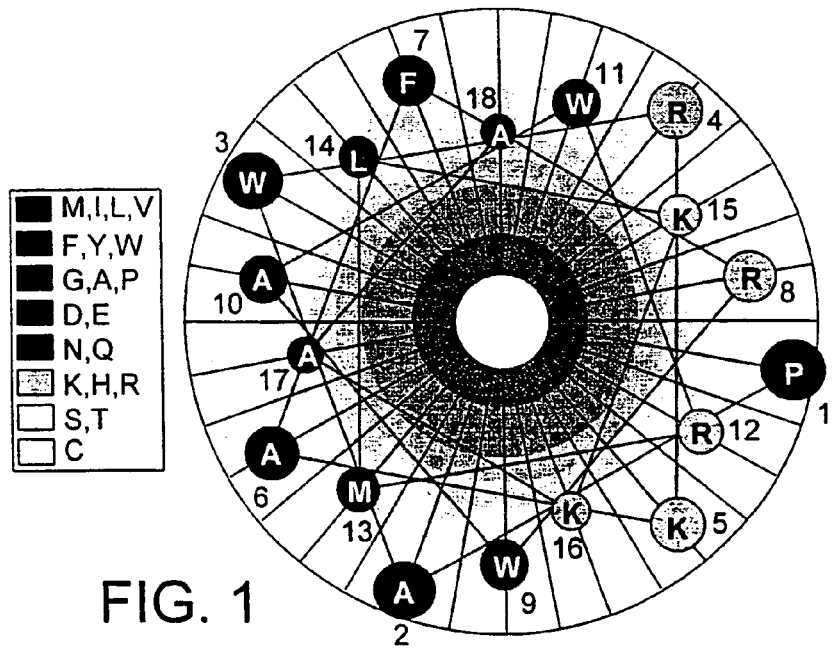
FIG. 1 shows a helical wheel representation of the peptide LFB 14-31m
Figure 2:
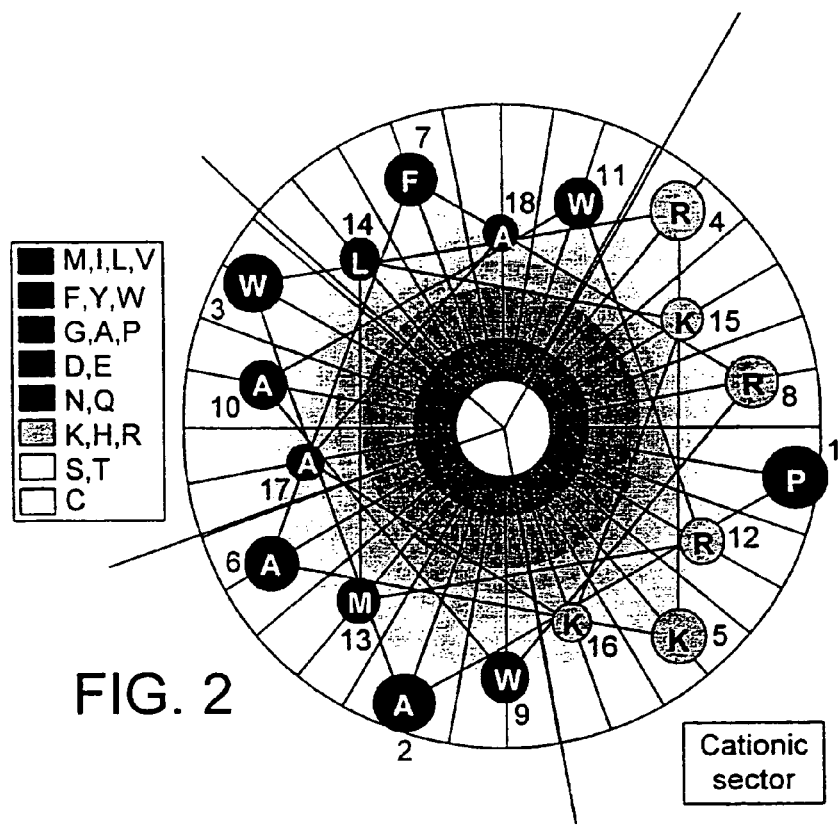
FIG. 2 shows a helical wheel representation of the peptide LFB 14-31m which has been divided into the 4 sectors in accordance with the invention.

The peptides were synthesised using Fmoc based chemistry on a fully automated Milligen 9050 synthesiser and purification and analysis using HPLC and electrospray mass spectrometry (VG Quattro Quadropole) was performed.

MIC (Minimum Inhibitory Concentration) Tests

The bacterial strains used were: *Escherichia coli* ATCC 25922 and *Staphylococcus aureus* ATCC 25923. All strains were stored at −70° C. The bacteria were grown in 2% Bacto Peptone water (Difco 1807-17-4). All tests were performed with bacteria in mid-logarithmic growth phase. Determination of the minimum inhibitory concentration (MIC) of the peptides for bacterial strains were performed in 1% Bacto Peptone water. A standard microdilution technique with an inoculum of $2 \times 10^6$ CFU/ml was used. All assays were performed in triplets. Since the peptides are positively charged and therefore could adhere to the plastic wells, we controlled the actual concentration of the peptides in the solution by HPLC. There was no difference between the concentration of the peptides before or after adding the solution to the plastic wells.

Anti-Tumour Activity

Meth A is a non-adhesive murine sarcoma cell line [Sveinbjørnsson et al, (1996) BBRC 223: 643-649] syngeneic in Balb/c and was maintained in vitro in RPMI 1640 containing 2% Foetal calf serum. Cells ($4 \times 10^6$) were applied in 96-well culture plates (Costar) in a volume of 0.1 ml RPMI 1640 medium. Peptide solutions (0.1 ml) were added and the plates incubated at 37° C. for 30 minutes, 4 hours or 24 hours. The cytotoxicity was measured using the MTT method (Mosmann et al., J. Immunol. (1986) 136, 2348-2357).

Fibroblast Assay

The MRC-5 cells to be used in the assay were grown to confluency to MEM containing 10% FBS, 1% L-glutamine and 0.1% penicillin and streptomycin. The cells were washed with PBS and then trypsinated using 2 ml trypsin (for a 80 cm culture flask). After the cells had detached from the wall, usually after ca 3 min. of incubation, 5 ml medium with FBS were added. The cells were resuspended and counted. The cells were then transferred to a centrifugation tube and spinned at 1500 rpm for 10 min. The supernatant was removed and the cells resuspended to a concentration of $1 \times 10^5$ cells/ml. 100 ul cells suspension was transferred to each well in a 96-well microtiter plate and incubated for 25 hours to allow the cells to attach.

Following the incubation, the medium containing serum was removed by turning the plate upside down against a piece of tissue. 100 ul medium without serum and L-glutamine (assay medium) was added to each well, and then removed as before. This was done to remove any trace of serum. The cells were stimulated by adding 100 ul of various concentrations of peptides diluted with assay medium to each well. The rest of the assay was done as previously described for methA, except that after the 2 hour incubation following MTT addition, 80 ul medium instead of 130 ul were removed.

Hemolytic Assay

The hemolytic activities of the peptides were determined using fresh human red blood cells. 8 ml blood was taken from a healthy person. 4 ml blood was transferred to a polycarbonate tube containing heparin to a final concentration of 10 U/ml, and the remaining 4 ml blood was transferred to a glass tube containing EDTA with final concentration of 15% EDTA. The erythrocytes were isolated from heparin-treated blood by centrifugation in 1500 rpm for 10 min and washed three times with phosphate-buffered saline (PBS) to remove plasma and buffy coat. The cell pellet was resuspended in PBS to make the final volume of 4 ml. The peptide was diluted to a concentration of 2 mg/ml and 0.1 mg/ml. The peptide was further diluted to the concentrations as stated in Table 1. For each tube PBS was added first, then RBCs and peptide solutions. The hematocrit in the blood treated with EDTA was determined after 30 min with Sysmex K-1000, and the resuspended RBCs were diluted into 10% hematocrit. RBCs in PBS (1%) with and without peptides (Table 18) were incubated in a shaker at 370 for 1 hour and then centrifuged at 4000 rpm for 5 min. The supernatant were carefully transferred to new polycarbonate tubes and the absorbance of the supernatant was measured at 540 nm. Baseline hemolysis was hemoglobin released in the presence of PBS, and 100% hemolysis was hemoglobin released in the presence of 0.1% Triton X-100.

Example 1

Figure 3:
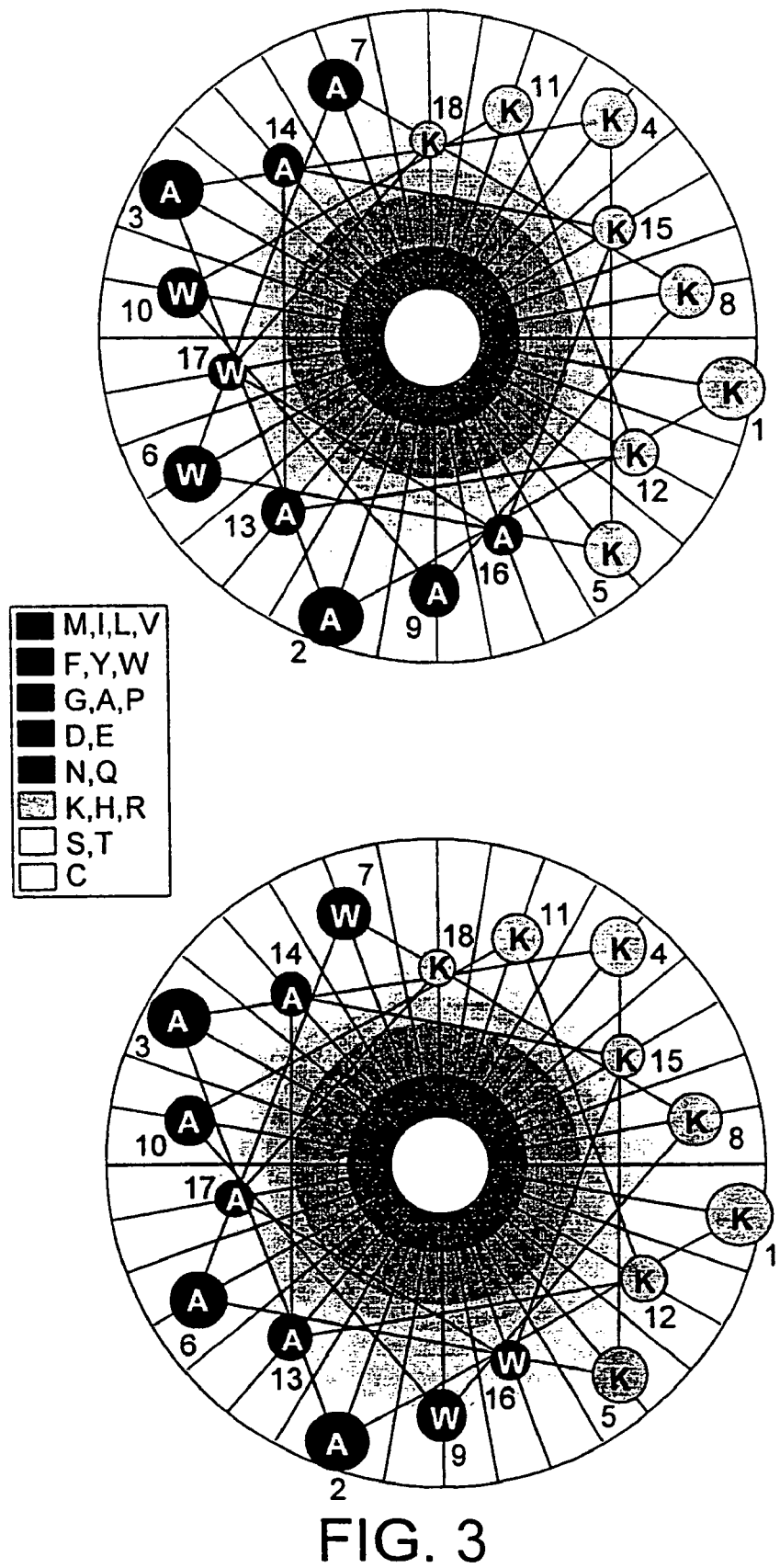
FIG. 3 shows helical wheels of two KA18 peptides tri-substituted by tryptophan.

The principles discussed herein were used in the design, synthesis and testing of peptides based on a perfectly amphipathic helical conformation comprising only alanine and lysine residues. The sequence of the starting peptide was as follows, KAAKKAA KAAKKAA KAAK referred to as "KA18". Modifications to this peptide to introduce one or more bulky and lipophilic residues were made by substituting Ala in flanking sector positions 7, 9 or 16 or in opposite sector positions 6, 10 or 17. Helical wheel representations of the two tri-substituted KA18 peptides are shown in FIG. 3.

Anti-tumoural activity was tested against Meth A cells and toxicity against red blood cells and normal fibroblasts. The results are shown in Table 1 below which illustrates the importance of bulky and lipophilic groups in the flanking but not opposite sectors.

| Peptide | $IC_{50}$ Meth A μM | $IC_{50}$ Fibroblast μM | $EC_{50}$ RBC μM |
|---|---|---|---|
| KA 18$W_{10}$ | >234 | >234 | >467 |
| KA 18$W_{16}$ | >234 | >234 | >467 |
| KA $W_{7,16}$ | >222 | >222 | >444 |
| KA 18$W_{6,10,17}$ | ≧211 | >211 | >422 |
| KA 18$W_{7,9,16}$ | 32 | >211 | >422 |

Example 2

As a model peptide we chose an analogue of lactoferricin B, an antimicrobial peptide derived from bovine lactoferrin. Based on the sequence 14-31 of bovine lactoferrin, this peptide was modified to give an ideal amphipathic helical structure with a narrow cationic sector. LFB (14-31)m is LFB 14-31$A_{2,6,10,17}F_7K_{16}L_{14}R_4$ (full sequence PAWRKAFR-WAWRMLKKAA). In this study one, two or all three of the Trp residues in the sequence were replaced by other amino acids, and the antibacterial, antitumoral and hemolytic activities were measured, as well as ability to inhibit fibroblasts.

Results

The sequences of the synthesised peptides and the activity data is summarised in Table 2.

The $IC_{50}/EC_{50}$ values are the concentration of peptide needed to kill 50% of the cells.

All the peptides were found to be homogenous by analytical HPLC and have the expected molecular weight as determined by FAB-MS.

Modelling of the Peptides

This peptide was chosen as a starting sequence in this study because it has high bioactivity against MethA, bacterial cells, RBCs as well as fibroblasts. FIG. 1 shows the helical wheel presentation of the peptide sequence. To start with, one by one of the 3 Trps, in position 3, 9 or 11, were replaced by Ala and Ile respectively. Following the single amino acid substitutions, two of the Trps, in position 9 and 11, were replaced by Ala and Ile, respectively. For the Ile replacement peptides we went further in investigating the substitution of Trps, and three additional peptides were synthezised in order to investigate all the combinations of substitutions possible.

Biological Activity of the Peptides

Antitumoral Activity

All of the Ala replacement peptides showed decreased activity compared to LFB(14-31)m. The most active, (14-31)mA11, with $IC_{50}$ of 11 μM, has a 1.5-fold decrease in activity. The decrease in activity was most profound when two of the 3 Trps, in position 9 and 11, were replaced. The most active of the Ile replacement peptides was (14-31)mI11, with $IC_{50}$ of 6 μM. Thus the activity of this peptide is slightly increased compared to LFB(14-31)m. Also in the Ile-replacement peptides the activity seems to decrease, however slightly, with two substitutions, similar to the results of the Ala and substitution peptides.

Antibacterial Activity

Compared to LFB(14-31)m all of the Ala replacement peptides had lower activity against *E. coli*, similar to the results obtained on MethA. The analogue with lowest activity against MethA, (14-31)mA9,11, also had lowest activity against bacteria.

The Ile replacement peptides show similar antibacterial activity compared to LFB(14-31)m, there are no major differences in activity between the different substitution analogues. Even (14-31)mI3,9,11, which had reduced MethA activity, did not show reduced antibacterial activity.

TABLE 2

| substitution | Peptide | Meth A $IC_{50}$ (μM)(4h) | Mic *E-coli* (μM) | Mic *S. Aureus* (μM) | RBC $EC_{50}$ (μM) | Fibroblast $IC_{50}$ (μM) |
|---|---|---|---|---|---|---|
| LFB (14-31)m | LFB 14-31$A_{2,6,10,17}F_7K_{16}L_{14}R_4$ | 6.6(J) | 2/4 | 2 | 110 | 17 |
| Alanine | | | | | | |
| W3→A3 | LFB 14-31$A_{2,3,6,10,17}F_7K_{16}L_{14}R_4$ | 24.1 | 6.9 | 4.6 | >463 | 190 |
| W9→A9 | LFB 14-31$A_{2,6,9,10,17}F_7K_{16}L_{14}R_4$ | 16.2 | 4.6 | 2.4 | 382 | 46.3 |
| W11→A11 | LFB 14-31$A_{2,6,10,11,17}F_7K_{16}L_{14}R_4$ | 11.1 | 4.6 | >1.2 | 278 | 46.3 |
| W9,11→A9,11 | LFB 14-31$A_{2,6,9,10,11,17}F_7K_{16}L_{14}R_4$ | 110.1 | 14.7 | 14.7 | >489 | >489 |
| Isoleucine | | | | | | |
| W3→I3 | LFB 14-31$A_{2,6,10,17}F_7K_{16}L_{14}R_4$ | 9 | 2/4 | 2/4 | 323 | 20 |
| W9→I9 | LFB 14-31$A_{2,6,10,17}F_7K_{16}L_{14}R_4$ | 12 | 5 | <1 | 155 | 26 |
| W11→I11 | LFB 14-31$A_{2,6,10,17}F_7K_{16}L_{14}R_4$ | 6 | 2/5 | <1 | 63.6 | 15 |
| W9,11→I9,11 | LFB 14-31$A_{2,6,10,17}F_7K_{16}L_{14}R_4$ | 22 | 35 | 19 | 284 | 26 |
| W3,9→I3,9 | LFB 14-31$A_{2,6,10,17}F_7K_{16}L_{14}R_4$ | 36 | 5 | 5 | >470 | 108 |
| W3,11→I3,11 | LFB 14-31$A_{2,6,10,17}F_7K_{16}L_{14}R_4$ | 16 | 2.5 | 5 | 413 | 45 |
| W3,9,11→I3,9,11 | LFB 14-31$A_{2,6,10,17}F_7K_{16}L_{14}R_4$ | 47 | 2.5 | 10 | >487 | 280 |

Hemolytic Activity

Ideally, antimicrobial/antitumoral peptides should have very low hemolytic activity, or the therapeutic window between the antimicrobial/antitumoral activity and the hemolytic activity should be considerable for the peptides to be considered as possible therapeutics. All but one of the LFB(14-31)m analogues, (14-31)mI11, had lower hemolytic activity than LFB(14-31)m indicating the important contribution of Trp for activity on red blood cells. Of the Ala replacement peptides, (14-31)mA9 and (14-31)mA11 had the highest activity, while (14-31)mA3 and (14-31)mA9,11 had the lowest activity.

Cytotoxicity

LFB(14-31)m was found to be highly toxic to fibroblasts, and thus there is no selectivity between these and MethA. The Ala replacement peptides vary considerably in activity, though none of them are more cytotoxic than LFB(14-31)m. Thus LFB (14-31)mA9,11, while being only moderately active against MethA, has no cytotoxic activity against red blood cells and fibroblasts. LFB(14-31)m A3 shows good activity against MethA cells and little toxicity against fibroblasts. Therefore removal of W3 in the opposite sector led to the highest selectivity.

Example 3

The peptides described in table 3 below were made and tested as described in the previous Examples.

Figure 4A:
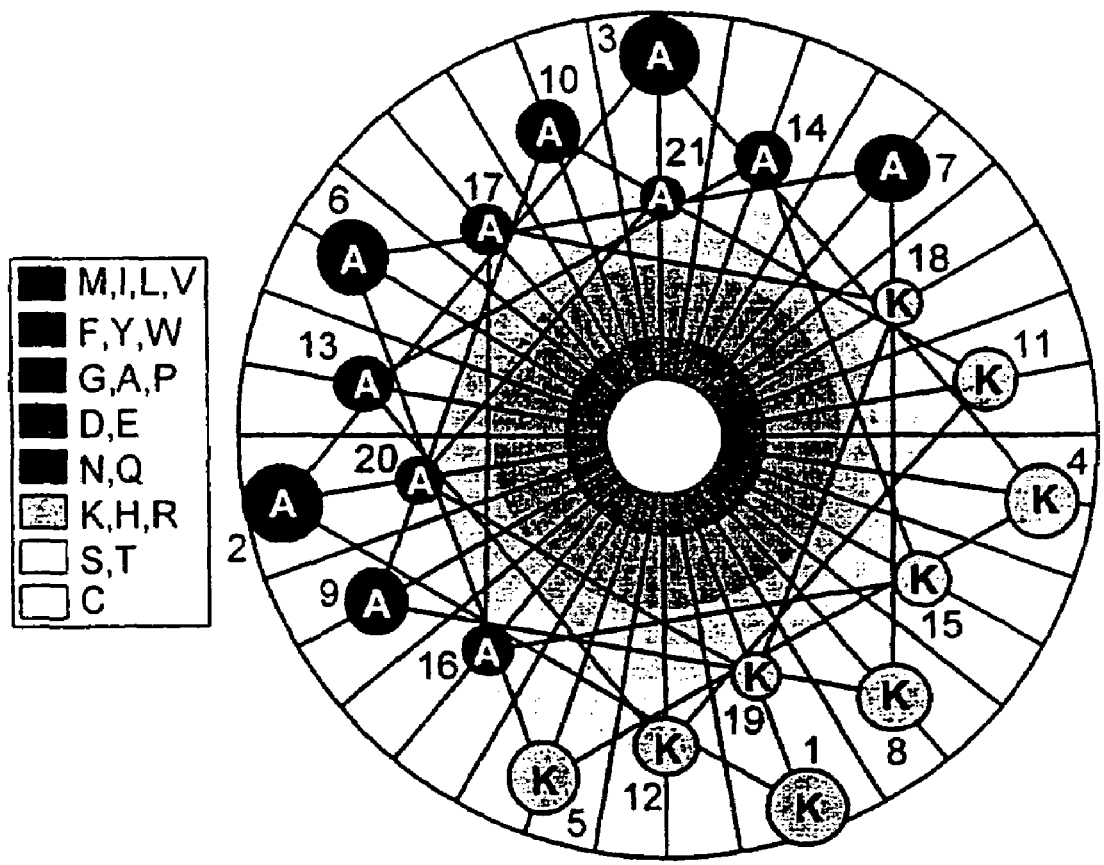
FIG. 4(*a*) shows helical wheel projections of the (KAAK-KAA) 3 peptide and (b) the same peptide substituted by 3 tryptophan residues or (c) 4 tryptophan residues.
Figure 4B:
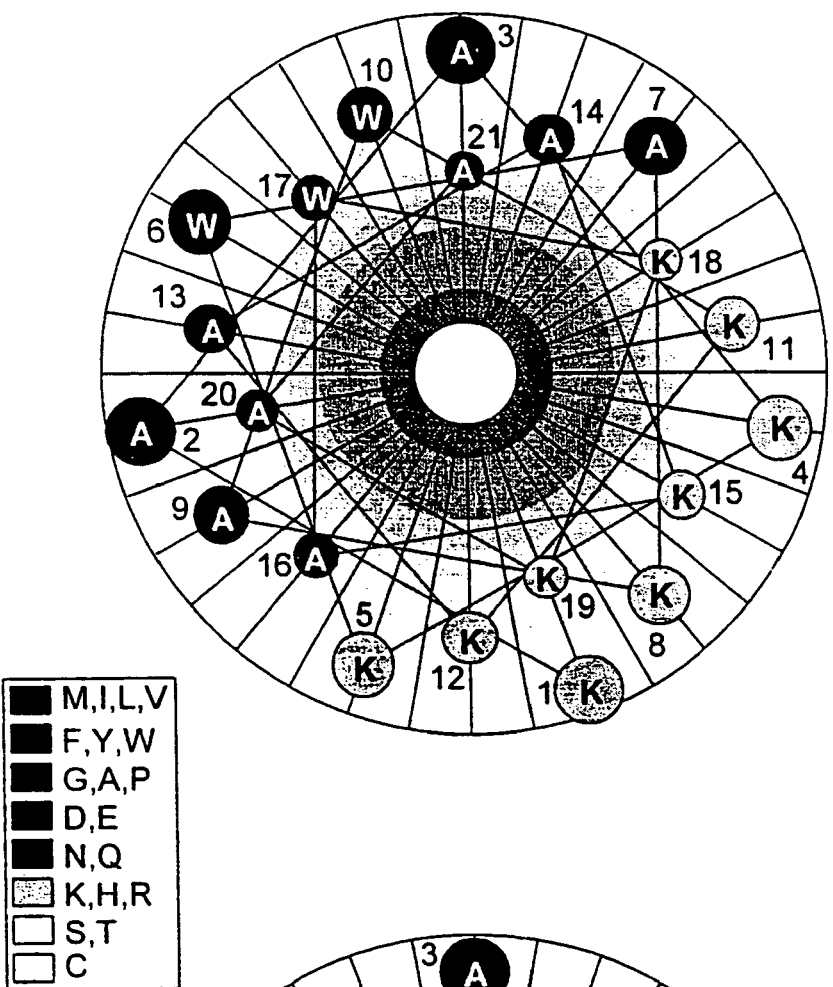
Figure 4B:
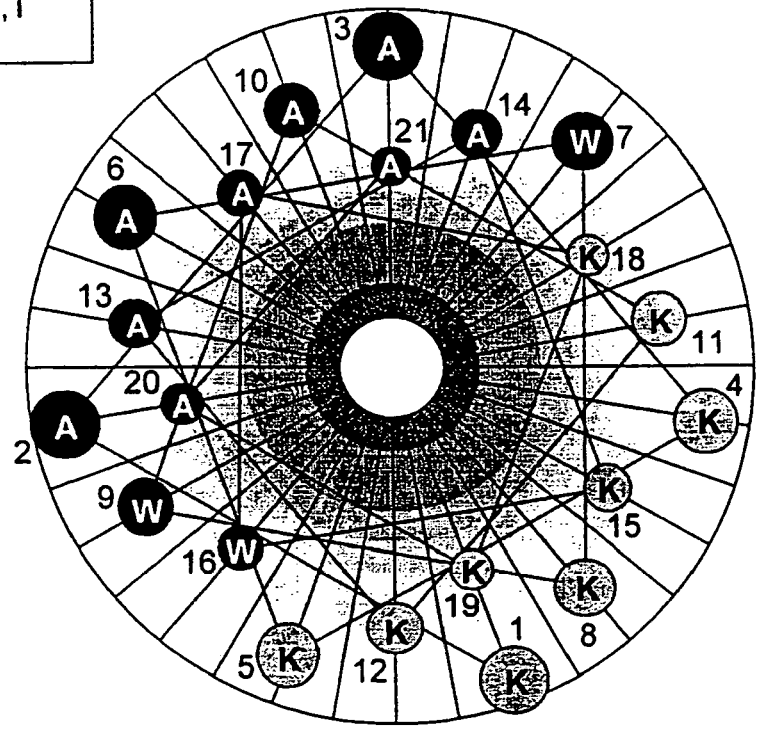
Figure 4C:
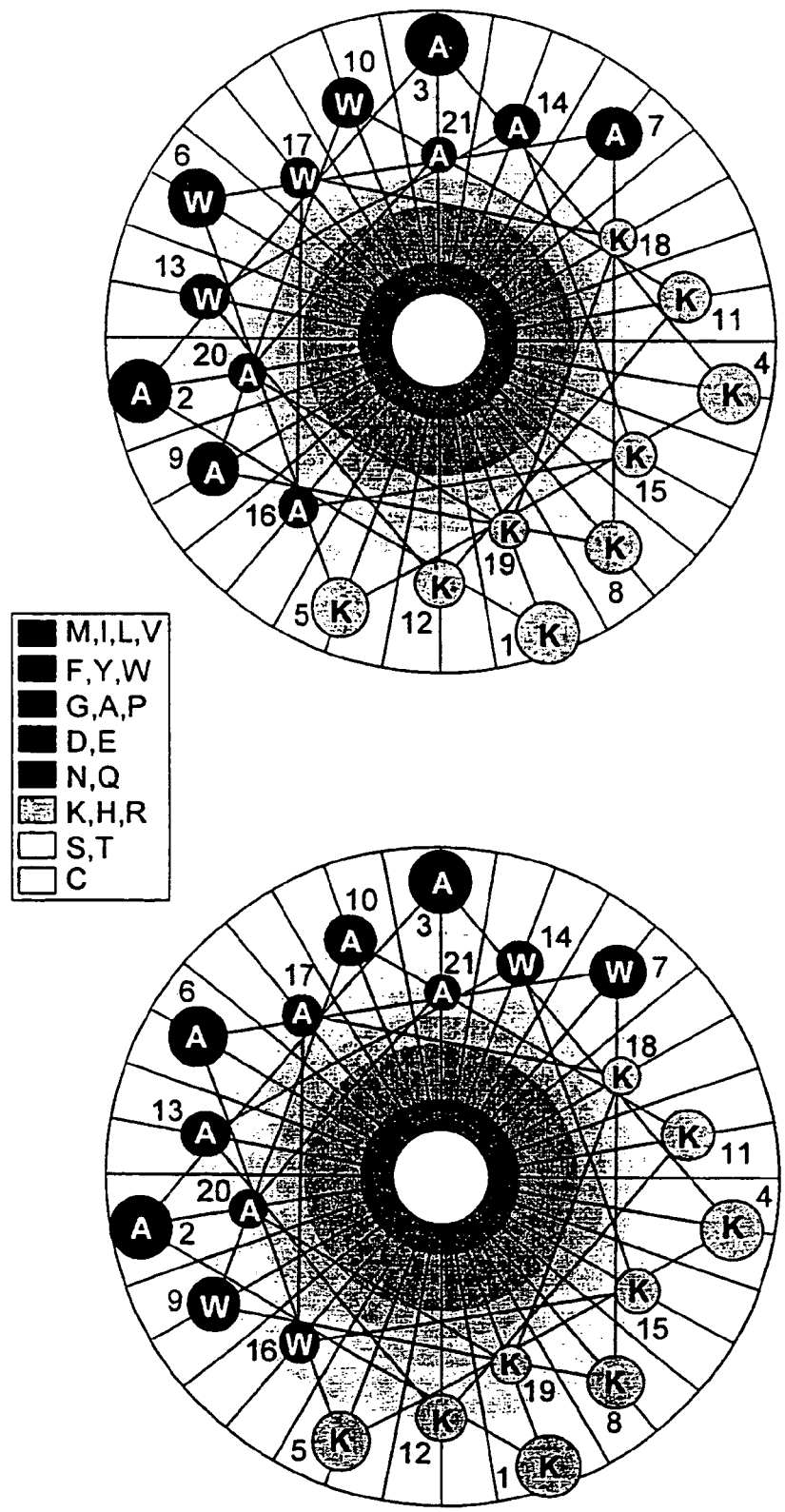

The model peptide (KAAKKAA)$_3$ has 9 lysine and 12 alanine residues and its amphipathic helical wheel configuration is shown in FIG. 4a. This de novo designed antimicrobial peptide with low mammalian toxicity was selected from the literature (Javadpour et al. J. Med. Chem. 1996, 39, 3107-3113. The MICs for this peptide against *E. coli* and *S. aureus* were 8 µM whereas it exhibited no measurable activity against fibroblasts or human erythrocytes.

| KA-peptide | Abbr. | Posit. | Meth A IC$_{50}$ | Fib IC$_{50}$ | RBC EC$_{50}$ | MIC *S. aur* | MIC *E. coli* | IC$_{50}$ Fib/MethA |
|---|---|---|---|---|---|---|---|---|
| 2 W | | | | | | | | |
| (KAAKKAA)$_3$ W$_{9,16}$ | KA 7 | 2F | >222 | >444 | >444 | 150 | 5 | |
| 3 W | | | | | | | | |
| (KAAKKAA)$_3$ W$_{7,9,16}$ | KA 3$_2$ | 1 + 2F | 28 | >422 | >422 | 15 | 5 | >15 |
| (KAAKKAA)$_3$ W$_{2,9,16}$ | KA 5 | 3F | 15 | 302 | >422 | 20 | 5 | 20 |
| (KAAKKAA)$_3$ W$_{6,10,17}$ | KA 3$_1$ | 3O | 147 | >422 | >422 | 35 | 10 | >3 |
| (KAAKKAA)$_3$ W$_{2,3,20}$ | KA15 | 1 + 2F | 16 | 246 | >422 | 10 | 7, 5- | 15 |
| (KAAKKAA)$_3$ W$_{7,10,17}$ | KA23 | 1F + 2O | 110 | >422 | >422 | | | >4 |
| (KAAKKAA)$_3$ W$_{7,16,17}$ | KA24 | 1 + 1F + 1 | 29 | >422 | >422 | | | >15 |
| 4 W | | | | | | | | |
| (KAAKKAA)$_3$ W$_{7,9,14,16}$ | KA 4 | 2 + 2F | 5 | 30 | >402 | 2, 5 | 2, 5- | 6 |
| (KAAKKAA)$_3$ W$_{2,3,20,21}$ | KA19 | 2 + 2 YF | 19 | 374 | >402 | | | 20 |
| (KAAKKAA)$_3$ W$_{2,9,16,20}$ | KA 8 | 4F | 4 | 23 | >402 | 5 | 5 | 6 |
| (KAAKKAA)$_3$ | KA 6 | 4O | 18 | >402 | >402 | 20 | 7, 5 | >22 |
| 4 F | | | | | | | | |
| (KAAKKAA)$_3$ F$_{2,9,16,20}$ | KA17 | 4F | 37 | >429 | >429 | 10 | 5- | >12 |

| | | | | | | | | |
|---|---|---|---|---|---|---|---|---|
| Bip | | | | | | | | |
| (KAAKKAA)$_3$ Bip$_{9,16}$ | KA27 | 2F | 24 | >429 | >429 | | | >18 |
| 18-mer | | | | | | | | |
| KKAWKWAKKAAWKWAKKA | KA18 | 2 + 2F | 8 | 115 | >451 | | | 14 |
| 15-mer | | | | | | | | |
| KKWAKKAWKWAKKAW | KA22 | 2 + 2F | 30 | >514 | >514 | | | >17 |
| WKWAKKAWKWAKKAA | KA21 | 2 + 2F | 32 | >530 | >530 | | | >17 |
| WKWAKKAAKWAWKAA | KA20 | 2 + 2F | 140 | 307 | >546 | | | 2 |
| Ornithine | | | | | | | | |
| (OAAOOAA)$_3$ W$_{7,9,14,16}$ | KA14 | 2 + 2F | 5 | 60 | >424 | 5 | 7.5-10 | 12 |

O=ornithine
Bip=biphenylalanine
Y=this indicates that the residues, although in the flanking sectors, are not immediately adjacent to the cationic sector The column head "Posit." indicates the number and position of residues either in the F=flanking or O=opposite sector. A measure of the selectivity of each peptide is shown by the Fib IC$_{50}$/Meth A IC$_{50}$ ratio.

These results show that for the 21aa peptides tested at least 3 Trp residues are required in order to achieve a significant lytic effect against the tumour cells. Three Trp residues provides better selectivity than 4 Trp residues as while the lytic effect against tumour cells is better with 4 Trp residues, the toxic effect as measured by the lytic effect against fibroblasts is also significantly increased. Clearly the optimum and minimum number of bulky and lipophilic groups in a given peptide will depend on the length of the peptide and the size of the particular bulky and lipophilic groups. Such optimisations can readily be performed by the skilled man on the basis of the guidance provided herein.

The degree of selectivity observed is surprising and therapeutically very encouraging.

Phenylalanine is less bulky and lipophilic than tryptophan and here 4 residues or more are required in order to achieve cytolytic activity in the 21aa peptide. By contrast biphenylalanine which is more bulky and lipophilic than tryptophan provides selectivity when only 2 residues are present.

The following peptides have also been made:

$(KAAKKAA)_3F_{7,9,14,16}$ $(KAAKKAA)_3F_{6,10,13,17}$ $(KAAKKAA)_3Bip_{10,7}$

The presence of lysine residues as the provider of cationic character is clearly not essential as a peptide wherein all the lysine residues are substituted by ornithine shows good activity. In fact, the shorter side chain of the ornithine residues has enhanced selectivity as compared to lysine.

The invention claimed is:

1. A method of producing a cytotoxic peptide, wherein said peptide is 7 to 25 amino acids in length, has at least 3 cationic amino acids and is capable of forming an amphipathic α-helix, which method comprises:
   a) representing the peptide as a 2-dimensional α-helical wheel,
   b) identifying a cationic sector and dividing the remaining part of the peptide into three further sectors which are substantially equal in size,
   c) incorporating into the sector which is opposite the cationic sector within the α-helical wheel representation of the peptide no more than 1 bulky and lipophilic amino acid,
   d) incorporating into the two sectors flanking the cationic sector 2 or more bulky and lipophilic amino acids, and
   e) synthesizing said peptide.

2. A method as claimed in claim 1 wherein one or more of the bulky and lipophilic amino acids is tryptophan or an analogue thereof.

3. A method as claimed in claim 1 or 2 wherein all of the bulky and lipophilic amino acids are tryptophan or analogues thereof.

4. A method as claimed in claim 1, or 2 wherein the peptide is 12 to 25 amino acids in length.

5. A method as claimed in claim 1, or 2 wherein the peptide comprises at least 7 cationic residues.

6. A method for the production of a pharmaceutical composition comprising a method of peptide production as claimed in claim 1 and mixing of the peptide prepared thereby with a pharmaceutically acceptable carrier.

7. A method as claimed in claim 1, or 2 wherein the peptide comprises at least 5 cationic residues.

8. A method as claimed in claim 3 wherein the peptide is 12 to 25 amino acids in length.

9. A method as claimed in claim 3 wherein the peptide comprises at least 7 cationic residues.

10. A method as claimed in claim 7 wherein the peptide comprises at least 7 cationic residues.

11. A method as claimed in claim 3 wherein the peptide comprises at least 5 cationic residues.

* * * * *

UNITED STATES PATENT AND TRADEMARK OFFICE
CERTIFICATE OF CORRECTION

| | | |
|---|---|---|
| PATENT NO. | : 7,393,824 B1 | Page 1 of 1 |
| APPLICATION NO. | : 10/069613 | |
| DATED | : July 1, 2008 | |
| INVENTOR(S) | : Rekdal et al. | |

It is certified that error appears in the above-identified patent and that said Letters Patent is hereby corrected as shown below:

On the title page, under (30) Foreign Application Priority Data, please add the following:

Aug. 31, 1999  (GB) ........................PCT/GB99/02851

Signed and Sealed this

Twenty-third Day of September, 2008

JON W. DUDAS
*Director of the United States Patent and Trademark Office*

SEQUENCE LISTING

```
<160> NUMBER OF SEQ ID NOS: 40

<210> SEQ ID NO 1
<211> LENGTH: 18
<212> TYPE: PRT
<213> ORGANISM: Artificial
<220> FEATURE:
<223> OTHER INFORMATION: modified bovine lactoferrin amino acid
      sequence, amino acids 14-31

<400> SEQUENCE: 1

Pro Ala Trp Arg Lys Ala Phe Arg Trp Ala Trp Arg Met Leu Lys Lys
1               5                   10                  15

Ala Ala

<210> SEQ ID NO 2
<211> LENGTH: 18
<212> TYPE: PRT
<213> ORGANISM: Artificial
<220> FEATURE:
<223> OTHER INFORMATION: modified bovine lactoferrin amino acid
      sequence, amino acids 14-31

<400> SEQUENCE: 2

Pro Ala Ala Arg Lys Ala Phe Arg Trp Ala Trp Arg Met Leu Lys Lys
1               5                   10                  15

Ala Ala

<210> SEQ ID NO 3
<211> LENGTH: 18
<212> TYPE: PRT
<213> ORGANISM: Artificial
<220> FEATURE:
<223> OTHER INFORMATION: modified bovine lactoferrin amino acid
      sequence, amino acids 14-31

<400> SEQUENCE: 3

Pro Ala Trp Arg Lys Ala Phe Arg Ala Ala Trp Arg Met Leu Lys Lys
1               5                   10                  15

Ala Ala

<210> SEQ ID NO 4
<211> LENGTH: 18
<212> TYPE: PRT
<213> ORGANISM: Artificial
<220> FEATURE:
<223> OTHER INFORMATION: modified bovine lactoferrin amino acid
      sequence, amino acids 14-31

<400> SEQUENCE: 4

Pro Ala Trp Arg Lys Ala Phe Arg Trp Ala Ala Arg Met Leu Lys Lys
1               5                   10                  15
```

Ala Ala

<210> SEQ ID NO 5
<211> LENGTH: 18
<212> TYPE: PRT
<213> ORGANISM: Artificial
<220> FEATURE:
<223> OTHER INFORMATION: modified bovine lactoferrin amino acid
      sequence, amino acids 14-31

<400> SEQUENCE: 5

Pro Ala Trp Arg Lys Ala Phe Arg Ala Ala Ala Arg Met Leu Lys Lys
1               5                   10                  15

Ala Ala

<210> SEQ ID NO 6
<211> LENGTH: 18
<212> TYPE: PRT
<213> ORGANISM: Artificial
<220> FEATURE:
<223> OTHER INFORMATION: modified bovine lactoferrin amino acid
      sequence, amino acids 14-31

<400> SEQUENCE: 6

Pro Ala Ile Arg Lys Ala Phe Arg Trp Ala Trp Arg Met Leu Lys Lys
1               5                   10                  15

Ala Ala

<210> SEQ ID NO 7
<211> LENGTH: 18
<212> TYPE: PRT
<213> ORGANISM: Artificial
<220> FEATURE:
<223> OTHER INFORMATION: modified bovine lactoferrin amino acid
      sequence, amino acids 14-31

<400> SEQUENCE: 7

Pro Ala Trp Arg Lys Ala Phe Arg Ile Ala Trp Arg Met Leu Lys Lys
1               5                   10                  15

Ala Ala

<210> SEQ ID NO 8
<211> LENGTH: 18
<212> TYPE: PRT
<213> ORGANISM: Artificial
<220> FEATURE:
<223> OTHER INFORMATION: modified bovine lactoferrin amino acid
      sequence, amino acids 14-31

<400> SEQUENCE: 8

Pro Ala Trp Arg Lys Ala Phe Arg Trp Ala Ile Arg Met Leu Lys Lys
1               5                   10                  15

Ala Ala

<210> SEQ ID NO 9
<211> LENGTH: 18
<212> TYPE: PRT
<213> ORGANISM: Artificial
<220> FEATURE:
<223> OTHER INFORMATION: modified bovine lactoferrin amino acid
      sequence, amino acids 14-31

<400> SEQUENCE: 9

Pro Ala Trp Arg Lys Ala Phe Arg Ile Ala Ile Arg Met Leu Lys Lys

<210> SEQ ID NO 10
<211> LENGTH: 18
<212> TYPE: PRT
<213> ORGANISM: Artificial
<220> FEATURE:
<223> OTHER INFORMATION: modified bovine lactoferrin amino acid
      sequence, amino acids 14-31

<400> SEQUENCE: 10

Pro Ala Ile Arg Lys Ala Phe Arg Ile Ala Trp Arg Met Leu Lys Lys
1               5                   10                  15

Ala Ala

<210> SEQ ID NO 11
<211> LENGTH: 18
<212> TYPE: PRT
<213> ORGANISM: Artificial
<220> FEATURE:
<223> OTHER INFORMATION: modified bovine lactoferrin amino acid
      sequence, amino acids 14-31

<400> SEQUENCE: 11

Pro Ala Ile Arg Lys Ala Phe Arg Trp Ala Ile Arg Met Leu Lys Lys
1               5                   10                  15

Ala Ala

<210> SEQ ID NO 12
<211> LENGTH: 18
<212> TYPE: PRT
<213> ORGANISM: Artificial
<220> FEATURE:
<223> OTHER INFORMATION: modified bovine lactoferrin amino acid
      sequence, amino acids 14-31

<400> SEQUENCE: 12

Pro Ala Ile Arg Lys Ala Phe Arg Ile Ala Ile Arg Met Leu Lys Lys
1               5                   10                  15

Ala Ala

<210> SEQ ID NO 13
<211> LENGTH: 21
<212> TYPE: PRT
<213> ORGANISM: Artificial
<220> FEATURE:
<223> OTHER INFORMATION: antimicrobial peptide

<400> SEQUENCE: 13

Lys Ala Ala Lys Lys Ala Ala Lys Ala Ala Lys Lys Ala Ala Lys Ala
1               5                   10                  15

Ala Lys Lys Ala Ala
            20

<210> SEQ ID NO 14
<211> LENGTH: 21
<212> TYPE: PRT
<213> ORGANISM: Artificial
<220> FEATURE:
<223> OTHER INFORMATION: modified antimicrobial peptide

<400> SEQUENCE: 14

Lys Ala Ala Lys Lys Ala Ala Lys Trp Ala Lys Lys Ala Ala Lys Trp

```
                1               5                  10                 15
Ala Lys Lys Ala Ala
            20

<210> SEQ ID NO 15
<211> LENGTH: 21
<212> TYPE: PRT
<213> ORGANISM: Artificial
<220> FEATURE:
<223> OTHER INFORMATION: modified antimicrobial peptide

<400> SEQUENCE: 15

Lys Ala Ala Lys Lys Ala Trp Lys Trp Ala Lys Lys Ala Ala Lys Trp
1               5                   10                  15

Ala Lys Lys Ala Ala
            20

<210> SEQ ID NO 16
<211> LENGTH: 21
<212> TYPE: PRT
<213> ORGANISM: Artificial
<220> FEATURE:
<223> OTHER INFORMATION: modified antimicrobial peptide

<400> SEQUENCE: 16

Lys Trp Ala Lys Lys Ala Ala Lys Trp Ala Lys Lys Ala Ala Lys Trp
1               5                   10                  15

Ala Lys Lys Ala Ala
            20

<210> SEQ ID NO 17
<211> LENGTH: 21
<212> TYPE: PRT
<213> ORGANISM: Artificial
<220> FEATURE:
<223> OTHER INFORMATION: modified antimicrobial peptide

<400> SEQUENCE: 17

Lys Ala Ala Lys Lys Trp Ala Lys Ala Trp Lys Lys Ala Ala Lys Ala
1               5                   10                  15

Trp Lys Lys Ala Ala
            20

<210> SEQ ID NO 18
<211> LENGTH: 21
<212> TYPE: PRT
<213> ORGANISM: Artificial
<220> FEATURE:
<223> OTHER INFORMATION: modified antimicrobial peptide

<400> SEQUENCE: 18

Lys Trp Trp Lys Lys Ala Ala Lys Ala Ala Lys Lys Ala Ala Lys Ala
1               5                   10                  15

Ala Lys Lys Trp Ala
            20

<210> SEQ ID NO 19
<211> LENGTH: 21
<212> TYPE: PRT
<213> ORGANISM: Artificial
<220> FEATURE:
<223> OTHER INFORMATION: modified antimicrobial peptide

<400> SEQUENCE: 19
```

-continued

Lys Ala Ala Lys Lys Ala Trp Lys Ala Trp Lys Lys Ala Ala Lys Ala
1               5                   10                  15

Trp Lys Lys Ala Ala
            20

<210> SEQ ID NO 20
<211> LENGTH: 21
<212> TYPE: PRT
<213> ORGANISM: Artificial
<220> FEATURE:
<223> OTHER INFORMATION: modified antimicrobial peptide

<400> SEQUENCE: 20

Lys Ala Ala Lys Lys Ala Trp Lys Ala Ala Lys Lys Ala Ala Lys Trp
1               5                   10                  15

Trp Lys Lys Ala Ala
            20

<210> SEQ ID NO 21
<211> LENGTH: 21
<212> TYPE: PRT
<213> ORGANISM: Artificial
<220> FEATURE:
<223> OTHER INFORMATION: modified antimicrobial peptide

<400> SEQUENCE: 21

Lys Ala Ala Lys Lys Ala Trp Lys Trp Ala Lys Lys Ala Trp Lys Trp
1               5                   10                  15

Ala Lys Lys Ala Ala
            20

<210> SEQ ID NO 22
<211> LENGTH: 21
<212> TYPE: PRT
<213> ORGANISM: Artificial
<220> FEATURE:
<223> OTHER INFORMATION: modified antimicrobial peptide

<400> SEQUENCE: 22

Lys Trp Trp Lys Lys Ala Ala Lys Ala Ala Lys Lys Ala Ala Lys Ala
1               5                   10                  15

Ala Lys Lys Trp Trp
            20

<210> SEQ ID NO 23
<211> LENGTH: 21
<212> TYPE: PRT
<213> ORGANISM: Artificial
<220> FEATURE:
<223> OTHER INFORMATION: modified antimicrobial peptide

<400> SEQUENCE: 23

Lys Trp Ala Lys Lys Ala Ala Lys Trp Ala Lys Lys Ala Ala Lys Trp
1               5                   10                  15

Ala Lys Lys Trp Ala
            20

<210> SEQ ID NO 24
<211> LENGTH: 21
<212> TYPE: PRT
<213> ORGANISM: Artificial
<220> FEATURE:
<223> OTHER INFORMATION: modified antimicrobial peptide

<400> SEQUENCE: 24

```
Lys Phe Ala Lys Lys Ala Ala Lys Phe Ala Lys Ala Ala Lys Phe
1               5                   10                  15

Ala Lys Lys Phe Ala
            20
```

<210> SEQ ID NO 25
<211> LENGTH: 21
<212> TYPE: PRT
<213> ORGANISM: Artificial
<220> FEATURE:
<223> OTHER INFORMATION: modified antimicrobial peptide
<220> FEATURE:
<221> NAME/KEY: MOD_RES
<222> LOCATION: (9)..(9)
<223> OTHER INFORMATION: Xaa=Biphenylalanine
<220> FEATURE:
<221> NAME/KEY: MOD_RES
<222> LOCATION: (16)..(16)
<223> OTHER INFORMATION: Xaa=Biphenylalanine

<400> SEQUENCE: 25

```
Lys Ala Ala Lys Lys Ala Ala Lys Xaa Ala Lys Lys Ala Ala Lys Xaa
1               5                   10                  15

Ala Lys Lys Ala Ala
            20
```

<210> SEQ ID NO 26
<211> LENGTH: 17
<212> TYPE: PRT
<213> ORGANISM: Artificial
<220> FEATURE:
<223> OTHER INFORMATION: antimicrobial peptide

<400> SEQUENCE: 26

```
Lys Lys Ala Trp Lys Trp Ala Lys Lys Ala Trp Lys Trp Ala Lys Lys
1               5                   10                  15

Ala
```

<210> SEQ ID NO 27
<211> LENGTH: 15
<212> TYPE: PRT
<213> ORGANISM: Artificial
<220> FEATURE:
<223> OTHER INFORMATION: antimicrobial peptide

<400> SEQUENCE: 27

```
Lys Lys Trp Ala Lys Lys Ala Trp Lys Trp Ala Lys Lys Ala Trp
1               5                   10                  15
```

<210> SEQ ID NO 28
<211> LENGTH: 15
<212> TYPE: PRT
<213> ORGANISM: Artificial
<220> FEATURE:
<223> OTHER INFORMATION: antimicrobial peptide

<400> SEQUENCE: 28

```
Trp Lys Trp Ala Lys Lys Ala Trp Lys Trp Ala Lys Lys Ala Ala
1               5                   10                  15
```

<210> SEQ ID NO 29
<211> LENGTH: 15
<212> TYPE: PRT
<213> ORGANISM: Artificial
<220> FEATURE:
<223> OTHER INFORMATION: antimicrobial peptide

<400> SEQUENCE: 29

Trp Lys Trp Ala Lys Lys Ala Ala Lys Trp Ala Trp Lys Ala Ala
1               5                   10                  15

<210> SEQ ID NO 30
<211> LENGTH: 21
<212> TYPE: PRT
<213> ORGANISM: Artificial
<220> FEATURE:
<223> OTHER INFORMATION: antimicrobial peptide
<220> FEATURE:
<221> NAME/KEY: MOD_RES
<222> LOCATION: (1)..(1)
<223> OTHER INFORMATION: Orn
<220> FEATURE:
<221> NAME/KEY: MOD_RES
<222> LOCATION: (4)..(5)
<223> OTHER INFORMATION: Orn
<220> FEATURE:
<221> NAME/KEY: MOD_RES
<222> LOCATION: (8)..(8)
<223> OTHER INFORMATION: Orn
<220> FEATURE:
<221> NAME/KEY: MOD_RES
<222> LOCATION: (11)..(12)
<223> OTHER INFORMATION: Orn
<220> FEATURE:
<221> NAME/KEY: MOD_RES
<222> LOCATION: (15)..(15)
<223> OTHER INFORMATION: Orn
<220> FEATURE:
<221> NAME/KEY: MOD_RES
<222> LOCATION: (18)..(19)
<223> OTHER INFORMATION: Orn

<400> SEQUENCE: 30

Xaa Ala Ala Xaa Xaa Ala Trp Xaa Trp Ala Xaa Xaa Ala Trp Xaa Trp
1               5                   10                  15

Ala Xaa Xaa Ala Ala
            20

<210> SEQ ID NO 31
<211> LENGTH: 21
<212> TYPE: PRT
<213> ORGANISM: Artificial
<220> FEATURE:
<223> OTHER INFORMATION: modified antimicrobial peptide

<400> SEQUENCE: 31

Lys Ala Ala Lys Lys Ala Phe Lys Phe Ala Lys Lys Ala Phe Lys Phe
1               5                   10                  15

Ala Lys Lys Ala Ala
            20

<210> SEQ ID NO 32
<211> LENGTH: 21
<212> TYPE: PRT
<213> ORGANISM: Artificial
<220> FEATURE:
<223> OTHER INFORMATION: modified antimicrobial peptide

<400> SEQUENCE: 32

Lys Ala Ala Lys Lys Phe Ala Lys Ala Phe Lys Lys Phe Ala Lys Ala
1               5                   10                  15

Phe Lys Lys Ala Ala
            20

```
<210> SEQ ID NO 33
<211> LENGTH: 21
<212> TYPE: PRT
<213> ORGANISM: Artificial
<220> FEATURE:
<223> OTHER INFORMATION: antimicrobial peptide
<220> FEATURE:
<221> NAME/KEY: MOD_RES
<222> LOCATION: (10)..(10)
<223> OTHER INFORMATION: Biphenylalanine
<220> FEATURE:
<221> NAME/KEY: MOD_RES
<222> LOCATION: (17)..(17)
<223> OTHER INFORMATION: Biphenylalanine

<400> SEQUENCE: 33

Lys Ala Ala Lys Lys Ala Ala Lys Ala Xaa Lys Lys Ala Ala Lys Ala
1               5                   10                  15

Xaa Lys Lys Ala Ala
            20

<210> SEQ ID NO 34
<211> LENGTH: 15
<212> TYPE: PRT
<213> ORGANISM: Artificial
<220> FEATURE:
<223> OTHER INFORMATION: Partial sequence of bovine lactoferricin B:
      LFB(17-31)

<400> SEQUENCE: 34

Phe Lys Cys Arg Arg Trp Gln Trp Arg Met Lys Lys Leu Gly Ala
1               5                   10                  15

<210> SEQ ID NO 35
<211> LENGTH: 18
<212> TYPE: PRT
<213> ORGANISM: Artificial
<220> FEATURE:
<223> OTHER INFORMATION: Artificial peptide of helical conformation

<400> SEQUENCE: 35

Lys Ala Ala Lys Lys Ala Ala Lys Ala Ala Lys Lys Ala Ala Lys Ala
1               5                   10                  15

Ala Lys

<210> SEQ ID NO 36
<211> LENGTH: 18
<212> TYPE: PRT
<213> ORGANISM: Artificial
<220> FEATURE:
<223> OTHER INFORMATION: Artificial peptide of helical conformation

<400> SEQUENCE: 36

Lys Ala Ala Lys Lys Ala Ala Lys Ala Trp Lys Lys Ala Ala Lys Ala
1               5                   10                  15

Ala Lys

<210> SEQ ID NO 37
<211> LENGTH: 18
<212> TYPE: PRT
<213> ORGANISM: Artificial
<220> FEATURE:
<223> OTHER INFORMATION: Artificial peptide of helical conformation

<400> SEQUENCE: 37

Lys Ala Ala Lys Lys Ala Ala Lys Ala Ala Lys Lys Ala Ala Lys Trp
1               5                   10                  15
```

```
Ala Lys

<210> SEQ ID NO 38
<211> LENGTH: 18
<212> TYPE: PRT
<213> ORGANISM: Artificial
<220> FEATURE:
<223> OTHER INFORMATION: Artificial peptide of helical conformation

<400> SEQUENCE: 38

Lys Ala Ala Lys Lys Ala Trp Lys Ala Ala Lys Lys Ala Ala Lys Trp
1               5                   10                  15

Ala Lys

<210> SEQ ID NO 39
<211> LENGTH: 18
<212> TYPE: PRT
<213> ORGANISM: Artificial
<220> FEATURE:
<223> OTHER INFORMATION: Artificial peptide of helical conformation

<400> SEQUENCE: 39

Lys Ala Ala Lys Lys Trp Ala Lys Ala Trp Lys Lys Ala Ala Lys Ala
1               5                   10                  15

Trp Lys

<210> SEQ ID NO 40
<211> LENGTH: 18
<212> TYPE: PRT
<213> ORGANISM: Artificial
<220> FEATURE:
<223> OTHER INFORMATION: Artificial peptide of helical conformation

<400> SEQUENCE: 40

Lys Ala Ala Lys Lys Ala Trp Lys Trp Ala Lys Lys Ala Ala Lys Trp
1               5                   10                  15

Ala Lys
```